(12) United States Patent
Tremolada

(10) Patent No.: US 11,389,616 B2
(45) Date of Patent: Jul. 19, 2022

(54) METHOD FOR PREPARING TISSUE, PARTICULARLY ADIPOSE TISSUE, FOR TRANSPLANTATION FROM LOBULAR FAT EXTRACTED BY LIPOSUCTION

(71) Applicant: LIPOGEMS INTERNATIONAL S.P.A., Milan (IT)

(72) Inventor: Carlo Tremolada, Milan (IT)

(73) Assignee: LIPOGEMS INTERNATIONAL S.P.A., Milan (IT)

( * ) Notice: Subject to any disclaimer, the term of this patent is extended or adjusted under 35 U.S.C. 154(b) by 572 days.

(21) Appl. No.: 16/381,925

(22) Filed: Apr. 11, 2019

(65) Prior Publication Data
US 2019/0232017 A1    Aug. 1, 2019

Related U.S. Application Data

(63) Continuation of application No. 15/264,320, filed on Sep. 13, 2016, now Pat. No. 10,286,178, which is a
(Continued)

(30) Foreign Application Priority Data

May 20, 2010   (IT) .......................... GE2010A000057

(51) Int. Cl.
*A61M 19/00*    (2006.01)
*C12M 1/33*    (2006.01)
(Continued)

(52) U.S. Cl.
CPC ............. *A61M 19/00* (2013.01); *A61B 17/34* (2013.01); *A61K 35/35* (2013.01); *A61M 1/815* (2021.05);
(Continued)

(58) Field of Classification Search
CPC ...... A61M 19/00; A61M 5/002; A61M 5/315; A61M 5/3286; A61M 2202/08;
(Continued)

(56) References Cited

U.S. PATENT DOCUMENTS

| | | |
|---|---|---|
| 3,526,321 A | 9/1970 | Flower |
| 5,079,160 A | 1/1992 | Lacy et al. |

(Continued)

FOREIGN PATENT DOCUMENTS

| | | |
|---|---|---|
| GB | 1356794 A | 6/1974 |
| JP | 05302010 A | 11/1993 |

(Continued)

OTHER PUBLICATIONS

European Search Report dated Nov. 4, 2016 in European Patent Application No. 16 18 2912.
(Continued)

*Primary Examiner* — Samuel G Gilbert
(74) *Attorney, Agent, or Firm* — Jeffrey N. Townes; Cozen O'Connor

(57) ABSTRACT

A method of preparing adipose tissue for transplantation, from lobular fat extracted, for instance, by liposuction, the fat including a fluid component that also includes an oily component, a blood component and/or sterile solutions and of a solid component that includes cell fragments, cells and one or more cell macroagglomerates of heterogeneous size, characterized in that it includes at least one step of forming an emulsion of the fluid component in the sterile washing solution by active and/or passive stirring and discharging the emulsion from the outlet through a density gradient.

7 Claims, 12 Drawing Sheets

Figure 1:
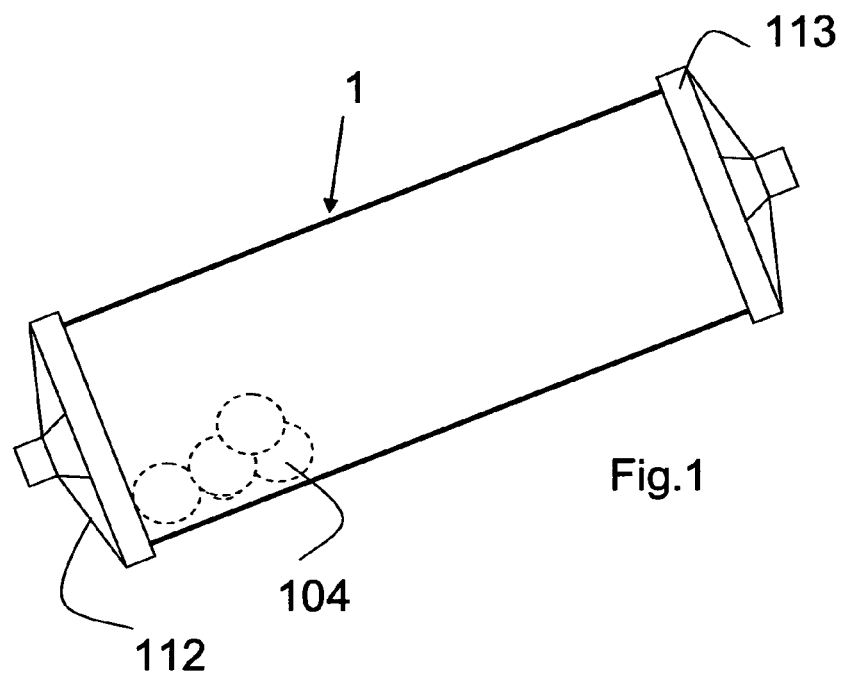

Related U.S. Application Data continuation of application No. 14/700,186, filed on Apr. 30, 2015, now Pat. No. 10,478,587, which is a continuation of application No. 13/698,400, filed as application No. PCT/JP2011/052204 on May 20, 2011, now Pat. No. 9,044,547.

(51) Int. Cl.

| | | |
|---|---|---|
| *C12M 1/00* | (2006.01) | |
| *A61M 1/00* | (2006.01) | |
| *A61M 5/00* | (2006.01) | |
| *A61M 5/315* | (2006.01) | |
| *B08B 3/10* | (2006.01) | |
| *A61B 17/34* | (2006.01) | |
| *C12N 5/077* | (2010.01) | |
| *A61K 35/35* | (2015.01) | |
| *A61M 5/32* | (2006.01) | |
| *B02C 19/00* | (2006.01) | |

(52) U.S. Cl.
CPC .............. *A61M 1/88* (2021.05); *A61M 5/002* (2013.01); *A61M 5/315* (2013.01); *A61M 5/3286* (2013.01); *B02C 19/0056* (2013.01); *B08B 3/102* (2013.01); *C12M 45/02* (2013.01); *C12M 47/04* (2013.01); *C12N 5/0653* (2013.01); *A61M 2202/08* (2013.01); *A61M 2202/09* (2013.01)

(58) Field of Classification Search
CPC ... A61M 2202/09; A61K 35/35; C12M 45/00; C12M 45/02; C12M 47/04; C12N 5/0653; B08B 3/102
See application file for complete search history.

(56) References Cited

U.S. PATENT DOCUMENTS

| | | | |
|---|---|---|---|
| 5,634,879 A | 6/1997 | Mueller-Glauser et al. | |
| 5,744,360 A | 4/1998 | Hu et al. | |
| 5,765,946 A | 6/1998 | Lott | |
| 5,786,207 A | 7/1998 | Katz et al. | |
| 5,804,366 A | 9/1998 | Hu et al. | |
| 6,020,196 A | 2/2000 | Hu et al. | |
| 6,316,247 B1 | 11/2001 | Katz et al. | |
| 7,140,239 B2 | 11/2006 | Greenwood et al. | |
| 7,595,043 B2* | 9/2009 | Hedrick ................. | C12N 5/069 424/93.7 |
| 7,637,872 B1 | 12/2009 | Fox | |
| 7,713,232 B2 | 5/2010 | Uber et al. | |
| 8,162,815 B2 | 4/2012 | Genovesi | |
| 8,246,947 B2 | 8/2012 | Hedrick et al. | |
| 8,361,042 B1* | 1/2013 | Gonzalez ............ | A61M 1/3695 604/317 |
| 8,366,694 B1 | 2/2013 | Jordan | |
| 9,453,202 B2 | 9/2016 | Harman et al. | |
| 9,624,462 B2 | 4/2017 | Sugiura | |
| 2003/0100105 A1 | 5/2003 | Poo et al. | |
| 2006/0083720 A1 | 4/2006 | Fraser et al. | |
| 2007/0184552 A1 | 8/2007 | Lynn | |
| 2007/0274960 A1 | 11/2007 | Harman et al. | |
| 2009/0193880 A1 | 8/2009 | Halverson et al. | |
| 2010/0285588 A1 | 11/2010 | Stubbers et al. | |
| 2013/0226187 A1 | 8/2013 | Schaller et al. | |

FOREIGN PATENT DOCUMENTS

| | | | |
|---|---|---|---|
| JP | 2003147125 A | 5/2003 | |
| JP | 3687975 B2 | 6/2005 | |
| JP | 2007508018 A | 4/2007 | |
| JP | 2009197338 A | 9/2009 | |
| JP | 2009294184 A | 12/2009 | |
| JP | 2010063441 A | 3/2010 | |
| WO | 2009073724 A1 | 6/2009 | |

OTHER PUBLICATIONS

European Search Report dated Jan. 28, 2013 in European Patent Application No. 12 197 925.6.
European Search Report dated Oct. 31, 2016 in European Patent Application No. 16 18 2908.
Office Action dated Oct. 7, 2017 in Japanese Patent Application No. 2013-510718.
Office Action dated Feb. 8, 2014 in Chinese Patent Application No. 201180034851.2.
Office Action dated Jul. 8, 2015 in Chinese Patent Application No. 201180034851.2.
Office Action dated May 15, 2017 in Canadian Patent Application No. 2,799,901.
Office Action dated Jul. 22, 2016 in European Patent Application No. 11 727 294.8.
Office Action dated Oct. 24, 2014 in Chinese Patent Application No. 201180034851.2.
Office Action dated Jul. 26, 2016 in European Patent Application No. 12 197 925.6.
Office Action dated Feb. 28, 2017 in European Patent Application No. 12 197 925.6.
Office Action dated Jan. 29, 2016 in Chinese Patent Application No. 201180034851.2.
Office Action dated Dec. 30, 2016 in Chinese Patent Application No. 201180034851.2.

* cited by examiner lipoaspirate and washing liquid

A: Washing step

B: Emulsion step

C: Emulsion removal step

Solid component on liquid

D: Solid component removal step

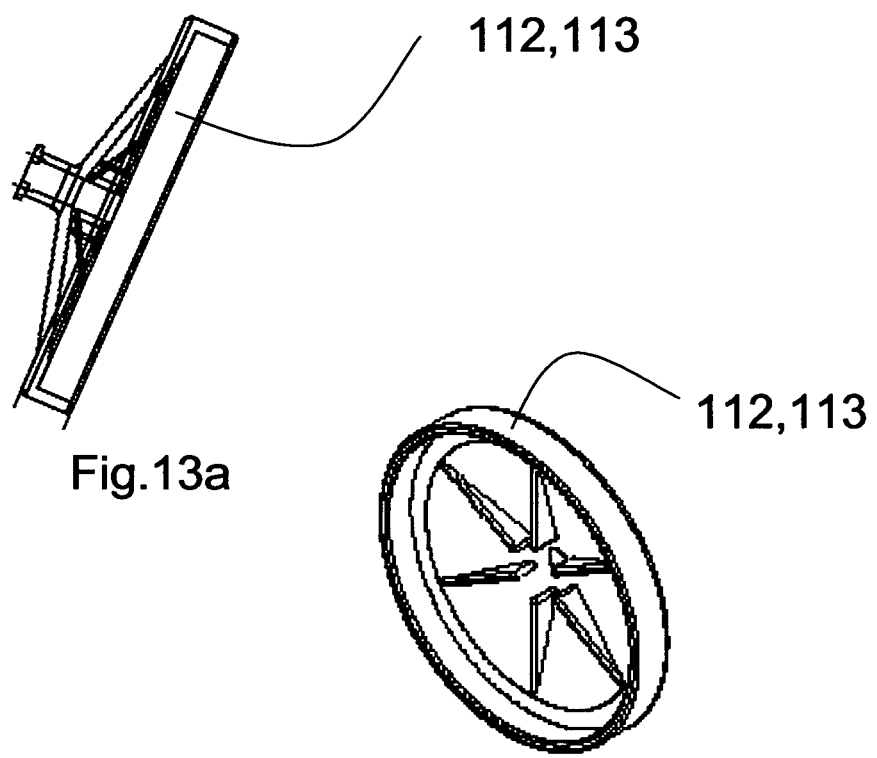
Fig.13a
Fig.13b
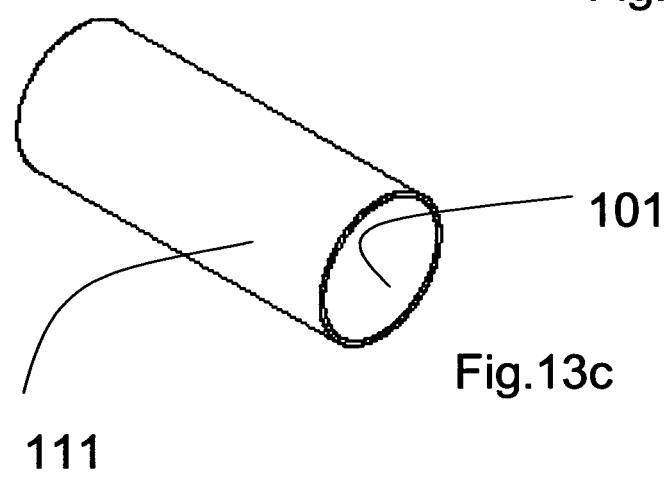
Fig.13c

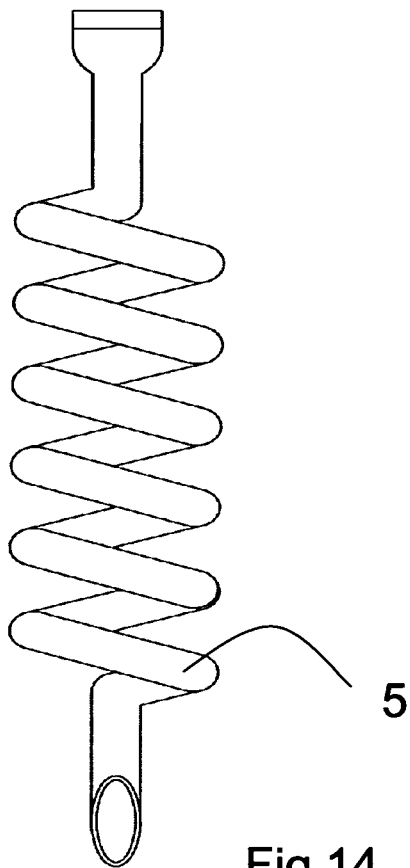
5
Fig.14
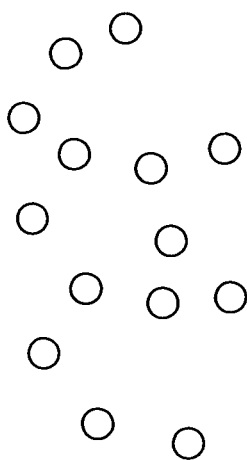

METHOD FOR PREPARING TISSUE, PARTICULARLY ADIPOSE TISSUE, FOR TRANSPLANTATION FROM LOBULAR FAT EXTRACTED BY LIPOSUCTION

This application is a continuation of U.S. patent application Ser. No. 15/264,320, filed Sep. 13, 2016, which is a continuation of U.S. patent application Ser. No. 14/700,186, filed on Apr. 30, 2015, which is a continuation of U.S. patent application Ser. No. 13/698,400, filed Jan. 22, 2013, now U.S. Pat. No. 9,044,547, which is a 35 U.S.C. § 371 U.S. National Stage application of International PCT Application No. PCT/IB2011/052204, filed May 20, 2011, which claims priority to Italian Patent Application No. GE2010A000057, filed May 20, 2010; all of which are hereby incorporated in their entirety.

The present invention relates to a method for preparing tissue, particularly adipose tissue, for transplantation, from lobular fat extracted by liposuction.

The invention also relates to a method of treating body and face volume deficiencies, improving skin trophism and/or for biological stimulation by the adipose tissue obtained through said method.

According to the prior art, the preparation required to reuse the liposuctioned material involves the separation of the vital cell component to be reinjected from the waste material composed of anesthetic liquid or biological fluids (serum or blood) and cell debris and oil resulting from the rupture of suctioned adipocytes.

Such separation may occur within the syringe that is used for withdrawal, or in special containers, essentially in three manners:
- by settling: the materials separate by differences in density under gravity,—by centrifugation: the materials separate by differences in density under the effect of centrifugal force,
- by washing: the lipoaspirate is placed in a thin-mesh strainer and washed, generally with a saline, that may be progressively replaced or not.

According to the best known technique (Coleman lipostructure), the syringes containing the lipoaspirate are closed at the bottom by a luer-lock cap, and are placed in a centrifuge for separating the liquid phase from the solid biological material.

Before using the biological material so obtained, the anesthetic and biological liquids left on the bottom of the syringe after centrifugation shall be manually drained, by removing the luer-lock cap from the syringe and causing them to flow out by gravity, whereas the cell fragments and oil resulting from the break of the cell walls of-adipocytes lie on the cell material to be transplanted and are removed in an incomplete and rudimentary manner, using gauzes that partially absorb the excess oil and often make the last part of the suctioned material unusable.

The above described technique suffers from certain drawbacks.

First, the step of suction and separation by centrifugation causes a considerable amount of adipocytes to break and release much oil, which cannot completely removed with the Coleman technique, and makes a significant portion of the lipoaspirate unusable, i.e. the portion of cell material that, after centrifugation, is located on the upper part of the syringe barrel, in contact with oil, and hence is contaminated by said oil.

This is because the presence of oil in the biological filler to be injected increases the risk of infections and rejections and causes increased inflammation.

Furthermore, the above described process involves multiple contacts of the liposuctioned material with surfaces of various types of instruments, as well as long-time contact with air in a potentially non-sterile environment, whereby use thereof in an operating room is recommended.

A technique is also known but rarely used, which involves mechanical fragmentation of the suctioned cell agglomerate using a blender, whose cutting blades separate fat lobules and provide an injectable cell suspension.

This fragmentation technique has many drawbacks.

First, the fragmentation step, which is followed by centrifugation, causes a considerable amount of adipocytes to break, which causes more than half of the liposuctioned material to be unusable for later aesthetic treatments. As a direct result, an increased number of liposuction sessions are required to compensate for this loss of material occurring during preparation of the material to be transplanted, with increased discomfort for patients.

Furthermore, the quantity of usable cell suspension that can be obtained using the above described procedure and devices largely depends on the skill of the health care staff in setting the speed and operating time parameters of the blender and the centrifuge and on the conditions of the instruments: an excessive rotation speed of the blades or the use, for example, of a blender with poorly cutting blades does not cause separation of fat lobules, but rather the mechanical break of the cell walls of a large amount of adipocytes, which involves oil formation and makes the cell suspension unusable, in addition to requiring accurate separation of the cell fragments and oil from the suspension. This is because the presence of oil in the biological filler to be injected increases the risk of infections and rejections.

Furthermore, the above described process involves multiple contacts of the liposuctioned material with surfaces of various types of instruments, as well as some contact with air in a non perfectly sterile environment, as is the case of doctor's offices. Since the material is of biological nature, extended contact with air or with multiple instruments, that may even not be perfectly sterile, increases the risk of bacterial or viral contamination, and may jeopardize treatment results.

The technique that involves washing through a strainer also has certain drawbacks.

Particularly the strainer net may easily become clogged with the liposuctioned material, which requires a. manual action to remove fat from. The meshes, thereby slowing down the preparation process and especially increasing the risk of contamination of the material to be injected.

The use of a simple strainer does not allow the liposuctioned material to be constantly maintained in a closed and perfectly sterile environment throughout the preparation process, i.e. from the liposuction step to the injection step.

Patent documents are known which disclose cell isolating devices.

The international application WO 2009/073724 discloses a method and an apparatus for isolating cells from lipoaspirate.

Particularly, it discloses a method for separating the adipocyte and oil fraction from the non-fat cell fraction in a lipoaspirate.

In order to obtain lipids and adipocytes that float on a cell solution of interest and other small cells within a container defined as "separation chamber", the adipose tissue is placed in a digestion chamber, and forced through a filter and through a head having pores into said "chamber".

The steps of washing the tissue, removing excess liquids, enzymatic digestion, antibiotic addition and cell selection may occur in a container defined as "digestion chamber". The digestion chamber may contain a filter that retains the tissue but allows the passage of dissociated cells and fluids. An aqueous emulsion containing adipocyte lipids is formed in this chamber.

The dissociated material in the digestion chamber may pass through a dispersing filter with pores smaller than the pores on the dispersing head contained in the first "separation chamber". This filter 115 is used to prevent clogging of the pores of the dispersing head.

In the "separation chamber" the lipids and adipocytes are separated from the cell population.

The device provides a cell population from a tissue without using the centrifuge but by forcing the solution through filters with pores of various sizes.

Said device is particularly complex in terms of construction, as shown in the figures.

Furthermore, the many passages of the organic material through chambers and filters extend the duration of the method, and expose the organic material to contamination risks.

Also, the complexity of the method and device make them unsuitable for use, for instance, in out-patient environments, which require quick preparation not injectable material from lipoaspirate and quick performance of face and body defect correction without the assistance of particularly specialized staff.

Furthermore, in this method, emulsions are formed using chemicals and not only through the use of mechanical means and forces.

US Application 2007/0274960 discloses a method of preparing a stem cell-containing composition. In order to prepare a stem cell population, in certain embodiments the liposuctioned adipose tissue is physically treated, i.e. cut or minced into smaller pieces, and undergoes enzymatic treatment, which facilitates release of the cells of interest from the other tissue components.

Therefore US 2007/0274960 allows the adipose tissue to be divided into smaller pieces by forcing it through an array of screens, to obtain smaller portions of uniform sizes, that can undergo enzymatic treatment in a more uniform manner, thereby providing a quicker release of stem cells and reducing the contact time between the released cells and the enzyme solution.

According to this patent, an emulsion of adipose tissue may be prepared using a perfluorocarbon solution, which emulsion is separable from the stem cells of interest.

The patent does not include the preparation of an emulsion of liquids that can be mechanically separated from lipid cells or small cell agglomerates. The container that contains the cutting means cannot be also used for injecting adipose tissue into a patient. U.S. Pat. No. 6,020,196 discloses a method for collecting microvascular endothelial cells.

The patent describes a method of treating suctioned adipose tissue, which adipose tissue, suctioned by a syringe with a cannula having apertures of such a size as to minimize stresses on cell components and to obtain a homogeneous adipose tissue, is forced from one syringe to another through a filter ('74) located between the suction ports of the two syringes.

By pulling the pistons of the syringes, the suctioned adipose tissue is homogenized by being forced through the filter from one syringe to another.

A lower viscosity of the suctioned material allows easier removal of the contaminants and improved digestion of the sample, for obtaining endothelial cells.

The method as disclosed in this patent suffers from certain drawbacks that make it unsuitable for use in the preparation of injectable fat, because:

the filter may become clogged by the adipose tissue: the filter-holding device forms a restriction in the flow line from one syringe to the other; the clogged filter obstructs the passage of adipose tissue from one syringe to the other and requires disconnection of the syringe and replacement of the filter to continue adipose tissue washing; due to these steps, the preparation of an emulsion of solid and liquid components becomes difficult and time-consuming and the organic material is exposed to contamination;

the passage through the filter" meshes for disintegration of the connective tissue also leads to the break of adipocytes, with formation of excess oil and the need for a later accurate separation of intact fat cells from oil.

U.S. Pat. No. 6,020,196 provides a homogenate from which endothelial cells may be extracted with the addition of collagenase and centrifugation, hence through the combination of chemical and physical actions. The patent does not involve the formation of an emulsion of liquid components upon which lipid cells or small agglomerates of lipid cells obtained from liposuctioned adipose tissue may float, which cells are directly injectable, after appropriate treatment, into a patient, without requiring particular sterile conditions of the environments, e.g. without requiring a perfectly sterile operating room.

U.S. Pat. No. 6,020,196 does not involve the possibility of providing a single device that, through a few simple treatment steps, allows preparation of the liposuctioned material and collection and temporary storage of fat, until reinjection.

Patent application US 2003/0100105 discloses an apparatus for extracting cells from organs. The apparatus includes a digestion chamber containing the organ and protease, and agitation means, such as balls having at least one cavity, which balls only act upon the organ.

Therefore, like the previous patents, this patent involves a chemically aggressive treatment of the organic material.

As described in column 3, paragraph 0026, the agitation means 14 are moved with the digestion chamber 12 to agitate the organ and facilitate the release of the cells.

The patent does not involve the possibility of obtaining an adipose tissue preparation for transplantation from lobular fat, particularly the patent involves the use of balls to agitate the organ and facilitate release of cells from said organ.

The object of the present invention is to provide a simple and inexpensive device, capable of obviating the above drawbacks, for preparing tissue, particularly adipose tissue for transplantation from lobular fat, i.e. fat composed of cell macroagglomerates, cells and cell fragments, which fat is obtained by means of liposuction.

The object of the present invention is to provide a device that can provide tissue for transplantation. without "using' chemicals for preparation, i.e. with no chemical aggression or any other chemical treatment of the lipoaspirate. This provides a simple and easy-to-use device, which only uses manually applied mechanical forces, which device may not require trials for' medical use, or only require simple trials. The device of the present invention may also be used in medical out-patient environments, without requiring particular sterile conditions, such as the conditions required in an operating room.

A further object of the present invention is a method that involves the use of said device for preparing tissue, particularly adipose tissue for transplantation, said method and device allowing the biological material to be maintained in a wholly closed system, i.e. a system that prevents any contact of the suctioned patient material with the outside environment.

Another object is also a method of treating body and face volume deficiencies, improving skin trophism and/or for biological stimulation by the adipose tissue obtained through said device and method.

Particularly, the device of the present invention allows preparation of cell agglomerates, particularly adipocyte agglomerates, using a few simple instruments and a few processing steps, without using chemicals or physico-chemical treatments, but only mechanical stirring, while eliminating most of the oily component and avoiding handling of the biological material in a non-perfectly sterile environment.

Thus, also due to the use of specially thin needles, the transplantation of adipose tissue will be less invasive, less traumatic and more effective.

Furthermore, the cell agglomerates yielded by the device of the present invention are prepared with minimized or no contact with the outside environment and using disposable instruments that reduce the risks of contamination of the biological material, the risks of instrument deterioration and the drawbacks associated with washing and re-sterilization.

The biological material so obtained may be injected into any tissue or organ.

The above objects are fulfilled by a device composed of at least one washing and separating container having a washing chamber for washing the liposuctioned material, which container has an inlet and an outlet for the liposuctioned material to enter the washing chamber through the inlet and for at least part of said material, particularly the fluid component, to exit said chamber through the outlet, said washing chamber including means for mechanically forming an emulsion of fluid components, on which the cell components designed to be used for later transplantation will float, separate from the liquid component.

Preferably, the tissue so prepared is used for autotransplantation, although the device may be also used for preparing tissues for allotransplantation.

The device and method of the present invention can provide not only adipose tissue for use as a biological filler, i.e. for correction of face and body volume deficiencies, but also macroagglomerates of adipose tissue having stem cells on their surface, whose arrangement in contact with the tissue of the injection area, allows quick regeneration of the treated tissues.

These means for mechanically forming an emulsion are capable of obtaining an emulsion of blood fluids, blood residues, oils and other solutions (such as washing saline solutions or anesthetic solutions used during suction), contained in the liposuctioned material, by simple mechanical action, allowing said fluids to remain separate from the solid cell material, i.e. lipid cells, stem cells.

The separation of the liquid phase to be eliminated from the solid phase to be transplanted is only obtained by a mechanical (and not a chemical) action.

In the preferred embodiment, this action is performed by stirring means, that may be of any type, particularly of active or passive type.

Active means are motorized stirring means, driven by a motor or a motive force to provide the stirring movement.

The passive means are means that exert their action upon stirring of the container, and hence operate, for example, by inertia.

The stirring means form an emulsion of the liquids to be eliminated and particularly fatty liquids, in a solvent such as a physiologic washing fluid. Especially in the embodiment with passive stirring means, the device has a very simple construction and is effective.

With this device, the mechanical action of the container, in combination with passive stirring means will not be of such strength as to require the use of mechanical means. Manual stirring is sufficient in the present device.

Preferably, the mechanical stirring action consists in a rotation of the container about an axis, e.g. a longitudinal axis, perpendicular to the end surfaces of the container, and either external or internal to the container. Other kinds of stirring may be also provided, such as shaking or the like.

These means for forming an emulsion by simple manual or possibly mechanical stirring of the washing and separating container, without using chemicals or enzymes that might lead to disintegration of the cell material, afford separation of the solid component from the liquid component in the washing chamber, and particularly allow the solid component, consisting of cell fragments, cells and cell aggregates, to float on an emulsion of liquid substances, such as blood, sterile solutions and oil yielded from broken fat cells. In a preferred embodiment, the solid component is washed in the washing chamber: a sterile washing solution, e.g. a sterile saline, is injected once or multiple times into the washing and separating container through the inlet. With stirring of the container, this solution allows the cell material for transplantation to be cleaned of any waste liquid, such as blood and oil.

The suctioned fat is composed of a mixture of fluid materials and cell fragments, cells and one or more cell macroagglomerates of heterogeneous size.

The emulsion formed upon stirring, due to the presence of mechanical emulsifying means in the washing chamber, is caused to exit from the outlet and be collected in a sealed container, to prevent contamination of the outside environment as well as to obtain cell material (cell fragments, cells, cell agglomerates) for transplantation, stored in the washing chamber in perfectly sterile conditions.

Then, said cell material is caused to exit the washing and separating chamber, and be injected or divided and stored, for later transplantation, into one or more sterile containers, such as syringes or the like.

Therefore an emulsion of waste liquids is simply formed, on which cell fragments, lipid cells, lipid microaggregates and stem cells float, which fragments or cells will be ready for use with no additional treatment, particularly with no chemical treatment.

The washing and separating container will be filled with lipoaspirate up to about ⅓ of its volume, the rest of the volume being filled with washing liquid.

There is no air in the container during treatment of the material.

The fat and/or the fat washing or treating liquids are forced through the device of the present invention by applying pressure or suction on the contents of said washing and separating and/or size reducing containers, i.e. on the material to be treated, through the use of compression means such as syringes connected to said containers, pistons that cooperate with the openings of said containers or the like.

Therefore, the device allows washing of the lipoaspirate and separation of the cell mass from the emulsion of fluid materials, such as washing solution, saline solution, anesthetic solution, blood and oil, so that a minimized amount of undesired impurities are collected at the end of the procedure with the cells or cell aggregates, particularly adipocytes.

With the device of the present invention, an emulsion is formed by mechanical means and particularly by washing, with elimination of the emulsion of liquid components through a density gradient.

The device may be used for washing lipoaspirate divided into smaller cells and/or agglomerates.

Techniques are known for dividing the liposuctioned material, e.g. by using a blender.

In a preferred embodiment, the liposuctioned material, particularly cell macroagglomerates are reduced to smaller sizes for easier transplantation.

According to the invention, in the washing and separating container or in another container, known as size reducing container, which is adapted to be fluid-tightly connected to said washing and separating container, size reducing means are provided for reducing the size of the solid component of the lipoaspirate, particularly cell magroagglomerates, to averagely equal smaller cell agglomerates, having a size equal to or smaller than a given value, which means consist of at least one series of parallel or intersecting sheets or cutting wires, to form at least one size reducing net, through which the liposuctioned material is passed.

In a preferred embodiment, homologation and/or size reduction of the lipoaspirate occurs before washing, by means of a first size reduction net, through which the liposuctioned material is forced before entering the washing chamber of the washing and separating container, and a second size reduction/homologation occurs by means of a second size reducing net, which size reduction is performed after at least one cell material washing step in the washing and separating container.

The second size reduction/homologation may occur at the end of the washing steps, before the exit of the material for transplantation from the washing and separating container.

Preferably the second size reducing net has narrower meshes than the first size reducing net.

Obviously, the material for transplantation may be caused to pass through multiple nets or size reducing means, particularly through two or more nets or size reducing means, said size reducing means being possibly provided in a single container or in two or more connectable washing and separating containers.

The first reduction facilitates washing as it fragments or stops the fibrous component of fat lobules and it homologates the size of the lipoaspirate mass by reducing it into smaller agglomerates, separate from each other and from the lipoaspirate itself. The second reduction provides a washed cell material ready for transplantation, whose size allows injection by any kind of needle, even of very small size.

The presence of at least two size reducing means, having meshes or apertures of different sizes, particularly larger meshes or apertures in the net located at the lipoaspirate inlet and smaller meshes in the net located at the outlet for the material ready for transplantation, and the provision of a given distance between said two means, i.e. at the end sides of the washing chamber, prevent said size reducing means from being clogged with the cell material, as size reduction occurs gradually.

Furthermore, such gradual size reduction of the lipoaspirate allows large needles to be possibly used during withdrawal of the tissue from donor areas, thereby speeding up the material collection procedure. Therefore, even when the liposuctioned material is composed of large agglomerates, it still doesn't clog the apertures or size reducing means of the device, as it is reduced into progressively smaller agglomerates, not by passing through a single size reducing mesh, net or sheet, but by sequentially passing through two or more size reducing means with meshes or apertures of decreasing sizes in the direction of the flow of the material to be treated.

Preferably, the cell material is reduced to a size allowing transplantation thereof through very thin needles after the end of the washing step/s.

The use of transplantation cannulae of particularly small size reduces the trauma caused by the transplantation procedure, and allows the latter to be performed under local anesthesia, with no suture or particular medication and with fast healing results.

Considering that the liposuctioned material also contains stem cells, fat size reduction provides small cell agglomerates, particularly microagglomerates of fat cells or individual cells, having stems cells adhered on their surface. The reduction of the lipoaspirate mass into many agglomerates provides a larger amount of stem cells potentially contacting the tissue to be treated upon injection of the material prepared by the method and the device of the present invention, as the size reducing action, in addition to reducing the suctioned mass into many equal smaller agglomerates, also causes an increase of the surface area potentially contacting the tissue to be treated, thereby increasing the exposure area with stem cells thereon.

The transformation of lobules of adipose tissue yielded by liposuction into a biological filler, i.e. a cell suspension or mass or a fluid or semifluid agglomerate containing adipocytes, other types of cells, such as stem or mesenchymal cells, and possibly cell fragments and residues of connective material, which suspension, at the end of the transformation procedure of the present application, has a solid phase composed of cells and/or cell aggregates of small, averagely homogeneous sizes, adapted to be injected in small or large amounts, allows the prepared fat to be used not only in an intra- or submuscular injection, but also in subcutaneous injections, without irregularities, hardening effects, calcifications and total reabsorption of the injected fat.

Nevertheless, the fat material may be injected into any tissue or organ.

Furthermore, the separation of fat lobules into small cells or cell agglomerates facilitates engraftment, i.e. integration of the cell mass in the tissues in which it is injected.

The division of fat lobules into cell aggregates also provides an increase of the surface of the injected cell mass that contacts the tissues undergoing transplantation, thereby promoting biological stimulation of treated tissues and hence integration of the injected cell material.

The use of a simple device, composed of a few sterile components, which isolate the extracted biological material from the external environment actually throughout the preparation procedure, considerably reduces the risk of contamination of the biological material, the personnel and the environment, and hence the risk: of infections or rejections during later use of the cell material.

Therefore, the device of the present invention also allows treatment of biological material outside operating rooms, in outpatient settings.

The simple construction of the device and the lack of any chemical and/or enzyme treatment of the lipoaspirate, except washing solutions leading to the formation of emulsions, can facilitate production and sales, and can avoid, facilitate or reduce the long and expensive research steps conducted to collect safety and effectiveness data about new drugs or new devices to obtain authorizations for use thereof.

Thus, the device and the method of the present invention afford a simple and quick procedure, for instance requiring a single outpatient session, for suction of fat from the body of a patient, treatment of said fat, with no chemical/enzyme emulsion of the lipoaspirate, and storage and/or reinjection thereof into a patient.

With the device of the present invention, having means therein, particularly balls, for forming an emulsion of liquids, a very short time is required to obtain emulsion of the liquids and separation of the solid cell material floating on said emulsion, by manual mechanical stirring.

The time required for treating the lipoaspirate and make it suitable for use is averagely 10 to 20 minutes; in any case, the time required for obtaining transplantable material is shorter than required with other prior art devices or methods.

The lipoaspirate storage and treatment device may be also used for the later transplantation step.

Otherwise, preferably, the treated material may be divided and transferred to other containers, for instance one or more 10 cc syringes, which containers may undergo settling and/or centrifugation, to separate the residual liquid/oily component from the solid component, which will be thus ready for transplantation, by subsequent transfer into one or more syringes of less capacity.

Therefore, the device of the present invention affords quick size reduction of adipose tissue clusters, allowing them to be injected through very small needles, leaving no visible scar on the patient (the prepared tissue may be used for face transplantation, where no large and visible holes would be aesthetically acceptable), and separate the emulsion/cell phases, to obtain injectable cells or cell agglomerates having a larger surface for the stem cells contained in the lipoaspirate, in contact with the tissues to be treated Reduction into small agglomerates allows activation of the peripheral stem cells lying on the outer surface of said agglomerates. The more agglomerates, the larger the exposed cell surface and the more peripheral stem cells potentially interacting with the treated tissues.

The method, device and kit as described in greater detail below may be used for treating not only lipid material but any kind of cell aggregate requiring cell aggregate size reduction and/or washing and separation of the liquid phase from the solid cell phase, simply by mechanical stirring.

Figure 2:
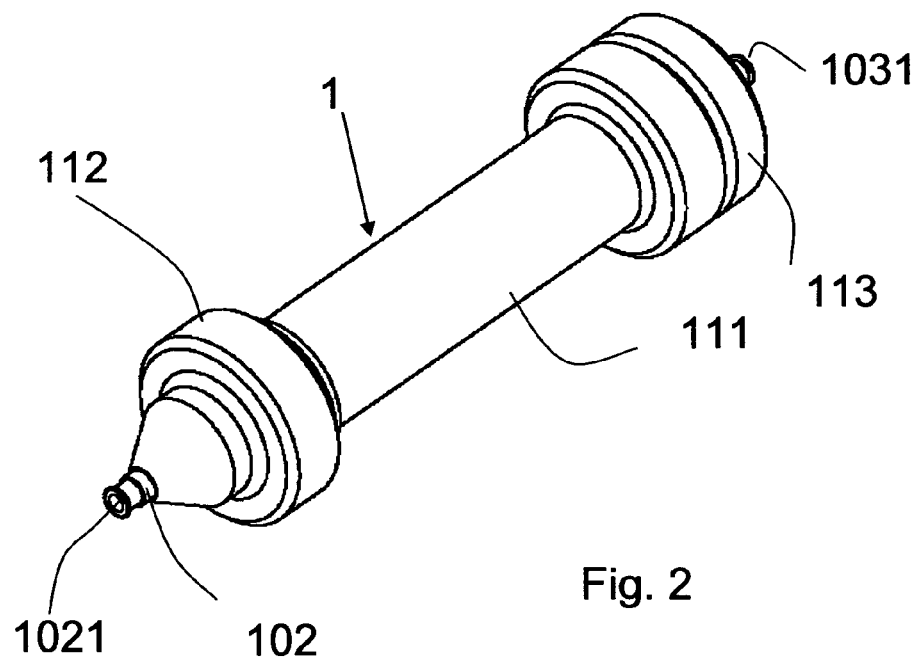
Figure 3:
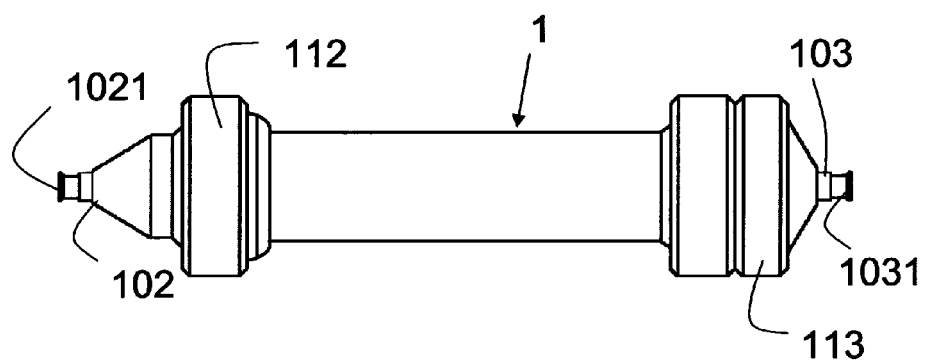
Figure 4:
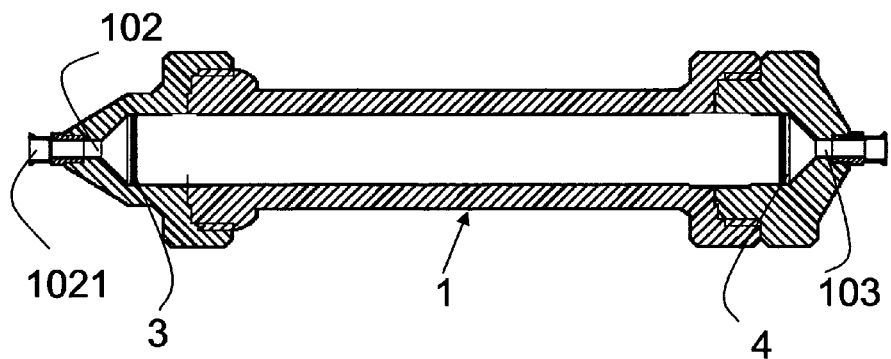
Figure 5:
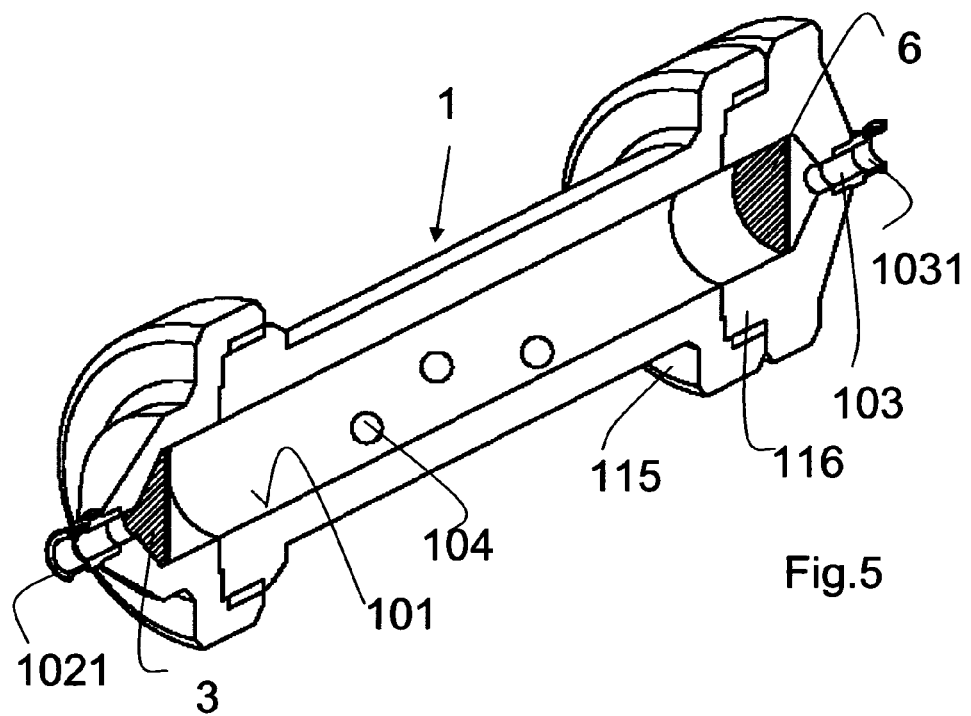
Figure 6:
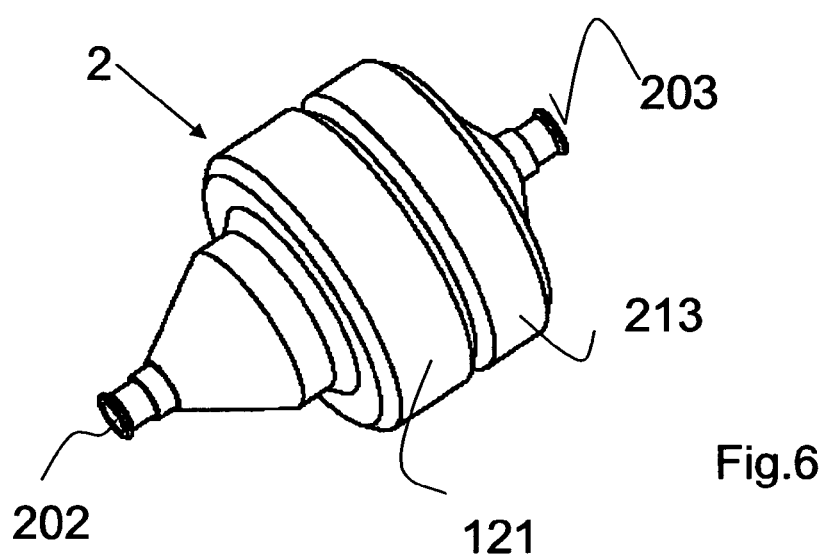
Figure 7:
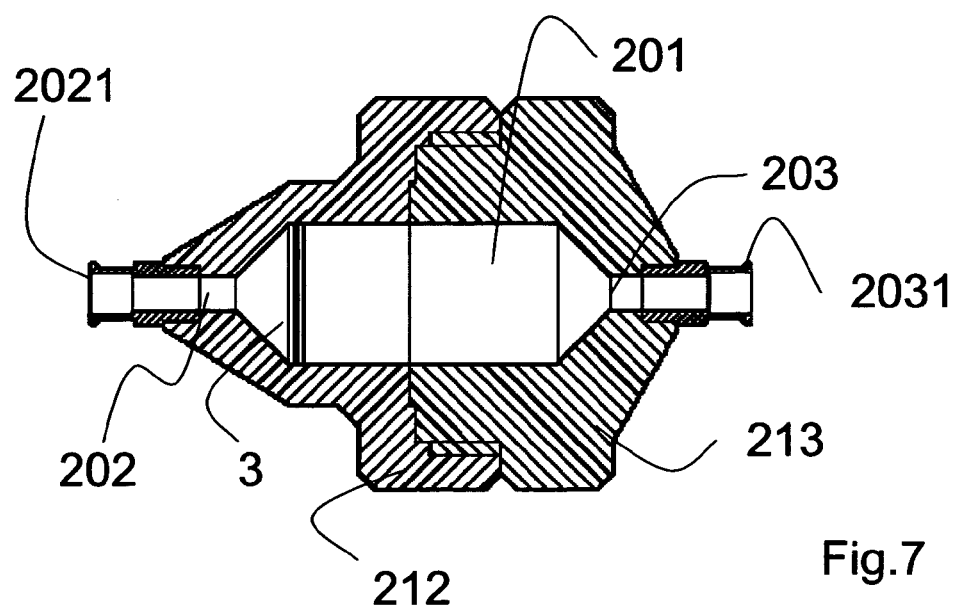
Figure 8A:
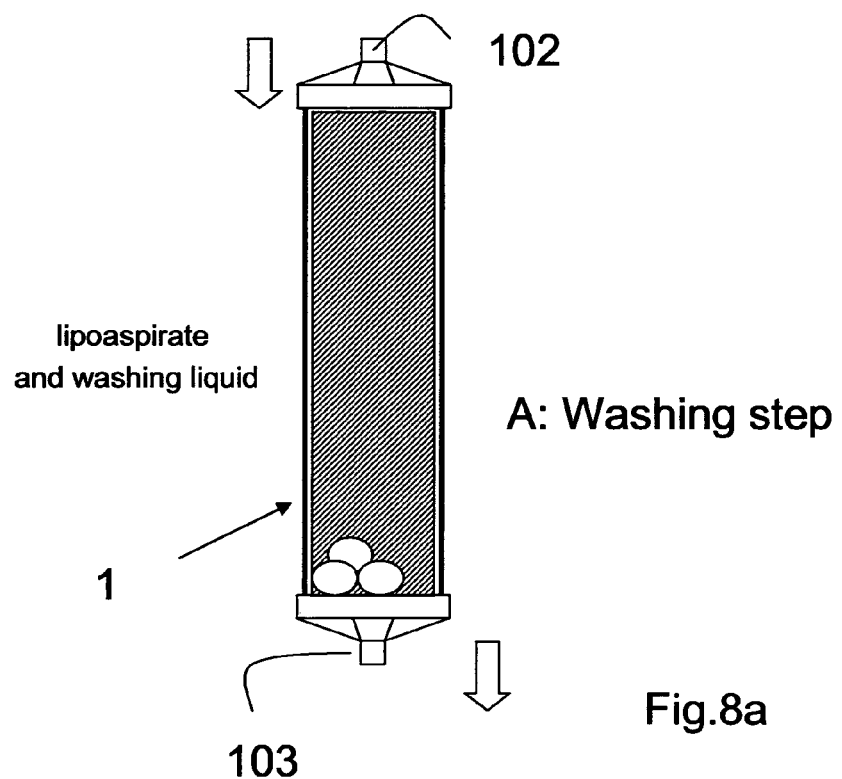
Figure 8B:
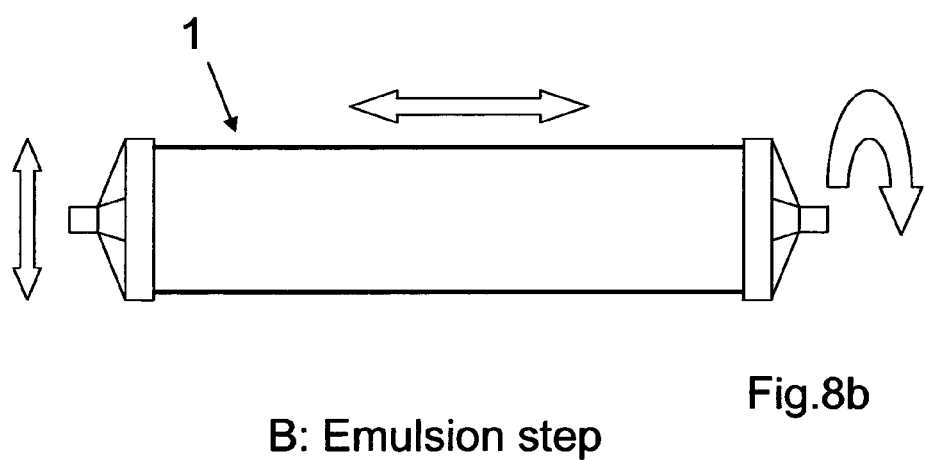
Figure 8C:
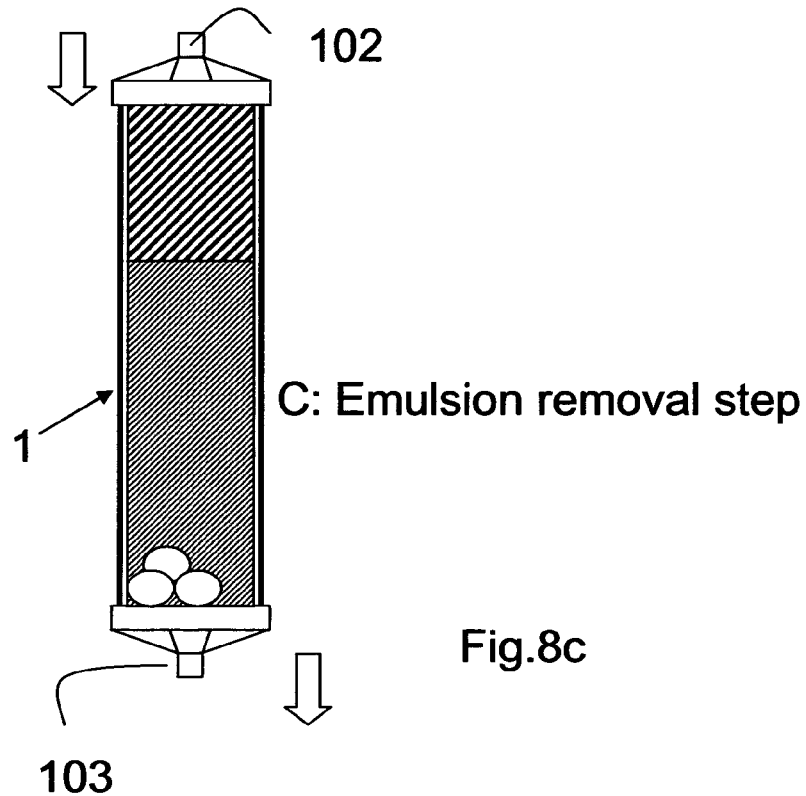
Figure 8D:
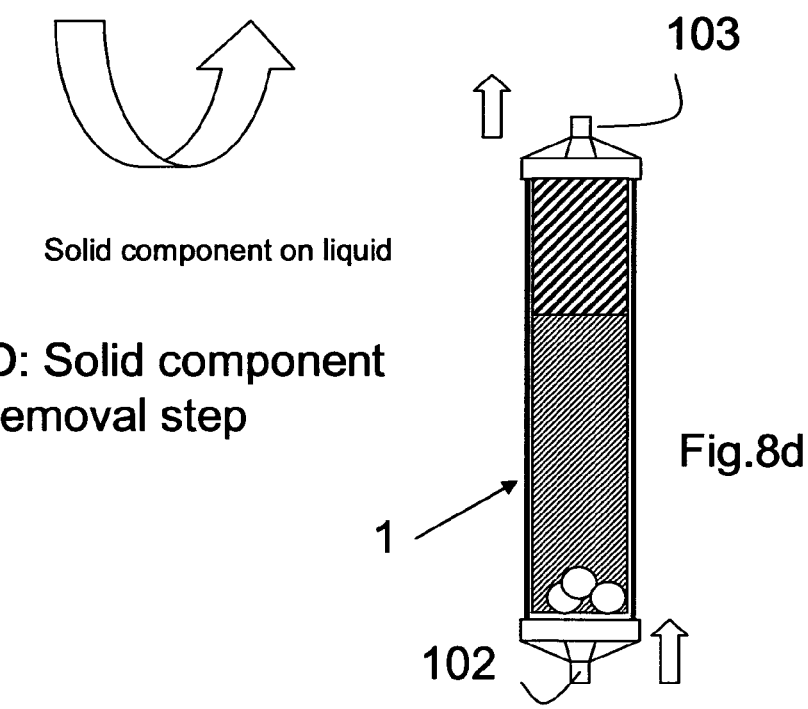
Figure 9:
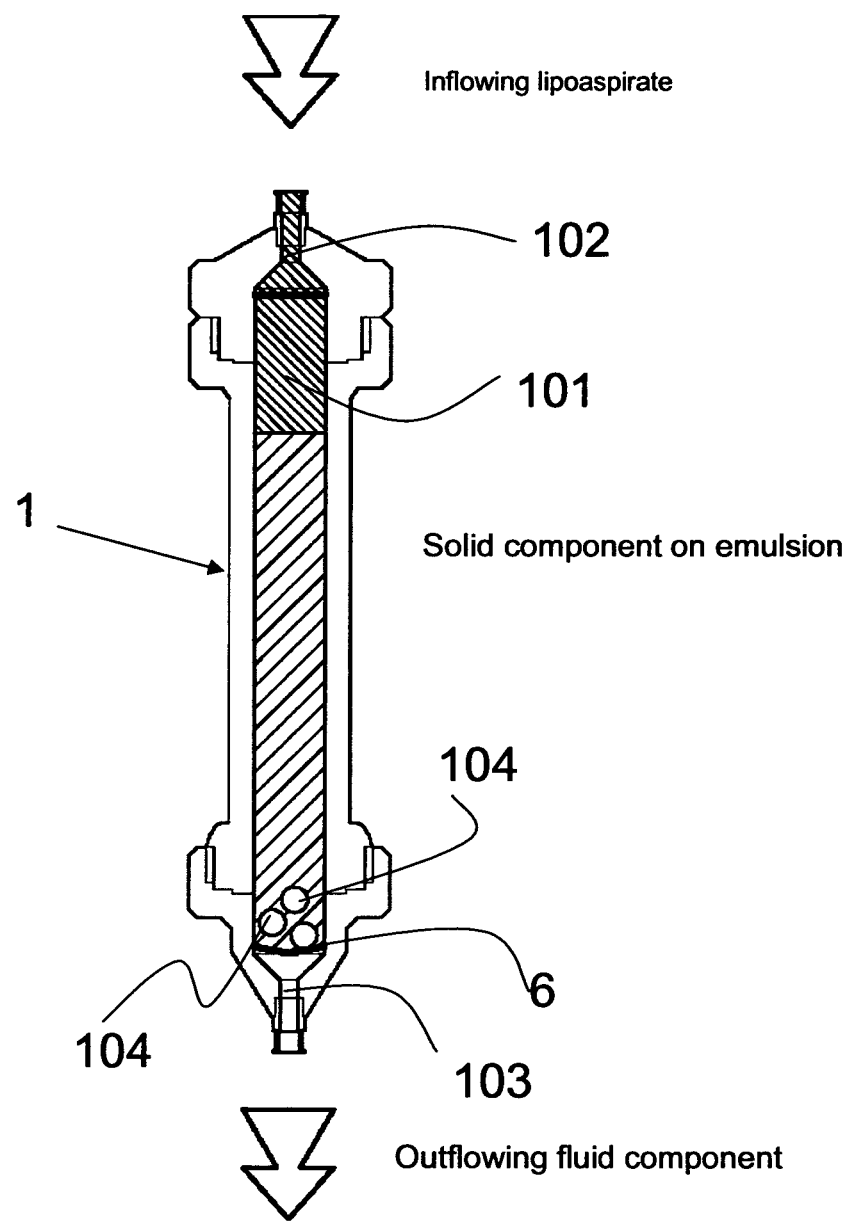
Figure 10:
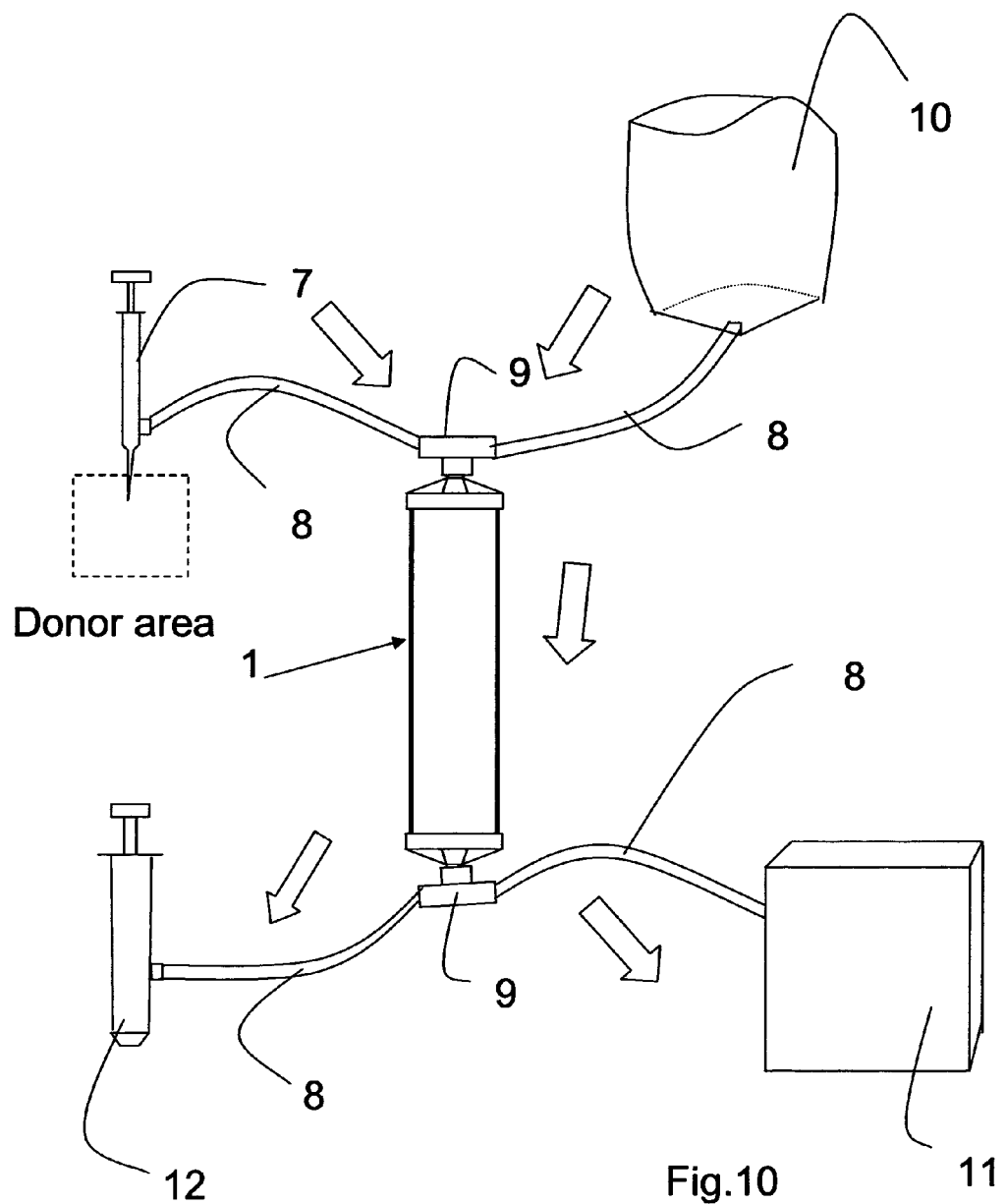
Figure 11A:
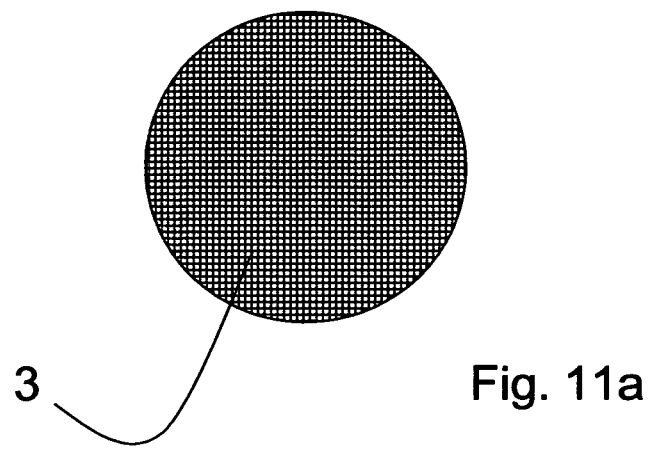
Figure 11B:
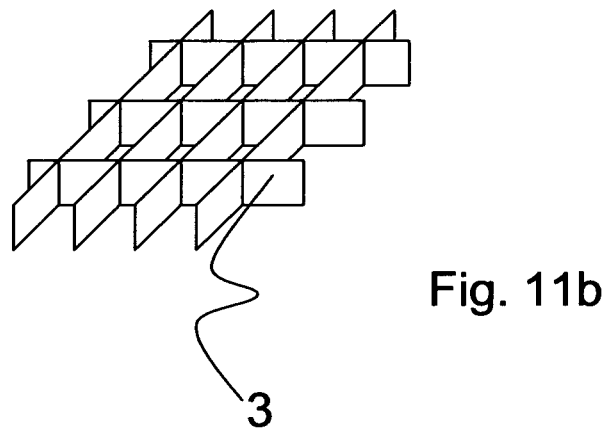
Figure 11C:
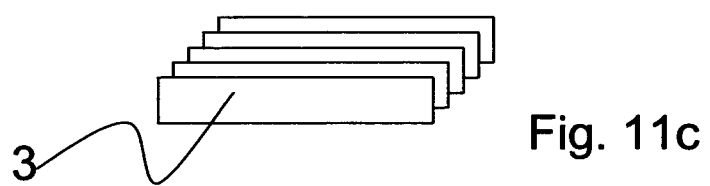
Figure 12A:
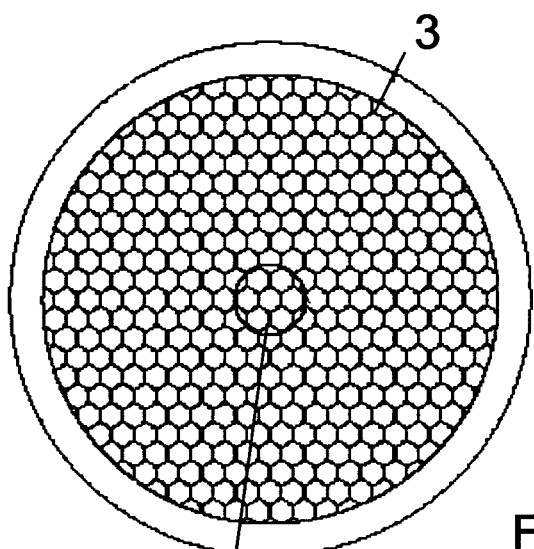
Figure 12B:
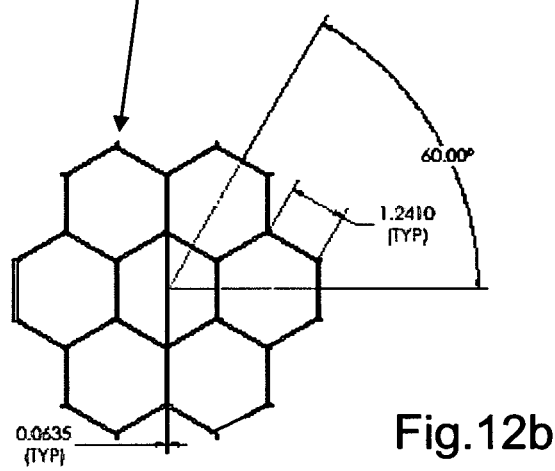

These and other features and advantages of the present invention will appear more clearly from the following description of a few embodiments, illustrated in the annexed drawings, in which:

FIG. 1 is a perspective view of the washing and separating container according to one embodiment, FIG. 2 is a perspective view of the washing and separating container according to a different embodiment, FIG. 3 is a side view of the washing and separating container, FIG. 4 is a longitudinal sectional view of the washing and separating container, with a filter located near the outlet, FIG. 5 is a longitudinally sectional view of the washing and separating container, having: a cell agglomerate size reducing net located near the inlet of the washing chamber, a second size reducing net located near the outlet, and stirring elements in the washing chamber, FIG. 6 is a perspective view of the size reducing container, FIG. 7 is a longitudinally sectional view of the size reducing container having a size reducing net near the inlet and a collection chamber for the reduced-size fat, FIGS. 8a-8d show the lipoaspirate treatment steps occurring in the washing and separating container, FIG. 9 is a longitudinally sectional view of the washing and separating container with the solid component floating on the emulsion of liquid components to allow the liquid component to exit from the outlet of the washing chamber, FIG. 10 shows the device of the present invention in the foreground, connected to ambulatory and/or surgical equipment, FIGS. 11a, 11b, 11c show embodiments of the size reducing means, FIGS. 12a, 12b show and embodiment of a size reducing net, with an enlarged detail, FIGS. 13a, 13b, 13c show and embodiment of the washing and separating container and the closing terminal, FIG. 14 shows a needle adapted for use in combination with the device, for transplantation of the prepared material.

The device of the present invention provides a cell suspension of adipose tissue to be used as a biological filler, i.e. a filler of natural and autologous or heterologous origin, during body and face volume correction procedures and/or during biological stimulation of any tissue or organ injected with said treated adipose material alone or with any other synthetic or natural filler.

The lobular fat material, i.e. the macroagglomerates of cells, particularly adipocytes, that are treated by the device of the present invention, may be obtained by means of a liposuction procedure which involves extraction of adipose tissue from any donor area of the patient, e.g. subcutaneous hip, abdomen or knee areas, under local anesthesia or generally in outpatient settings.

Once said adipose tissue has been treated with the device of the present invention, it can be used for autotransplantation, i.e. injection into special areas of the body of the patient from which the tissue has been withdrawn, to fill areas that, due to aging, diseases, treatments, e.g. radiotherapy; or past surgery, exhibit volume deficiencies or reabsorption of subcutaneous fat, with the relevant part of the body being sunken, with projecting bones and sagging skin.

The tissue treated with the device and method of the present invention maybe arranged to be used on receiving patients other than the donor patient.

An exemplary liposuction procedure will be now described.

The liposuction procedure includes preparation of the anesthetic liquid, appropriately diluted and possibly added with vasoconstrictive adrenaline, in sterile syringes, preferably having a needle or cannula connector known as luer connector, with the barrel volume suitable for the surface area of the body to be anesthetized, for instance 10 to 60 cc syringes.

Once the areas for withdrawal of adipose tissue have been marked and suitably disinfected, the local anaesthetic liquid is injected through sterile disposable blunted-end cannulas of about 1 mm diameter, preferably having a luer connector.

The patient's skin is sterilized with conventional techniques and anesthetized by a wheal.

Anesthesia is obtained by introducing the anesthetic solution through progressive introduction of the disposable blunted-end sterile cannula through the skin into the subcutaneous tissue to impregnation of the entire target area with the anesthetic.

For anaesthetic injection and later insertion of the needle or cannula for adipose tissue withdrawal, the skin may be perforated by a sterile pointed needle or a sterile lanceolate blade of sufficient diameter to allow later introduction of the disposable withdrawal cannula.

I If needed, the patient may be sedated.

Liposuction, i.e. withdrawal of adipose tissue is performed with a sterile syringes connected to a cannula, preferably having multiple holes with a diameter ranging from 1.2 to 3 mm. Cannulas of up to 6 mm diameter may be also used.

With the device of the present invention, large diameter cannulas (preferably 3 mm multi-hole cannulas) may be used for withdrawal, allowing quick extraction of a large amount of adipose tissue, because the macroagglomerates of cells so extracted will be subjected to size reduction before use, as described in greater detail below. In one embodiment, said syringe, having at least a 10 cc volume, has a luer connector for connection to a disposable sterile cannulas, which cannulas have one or more holes over their surfaces for suction of the tissue.

Obviously, the volume of the suction syringe and the suction cannula depends on the amount of adipose tissue to be suctioned, which in turn depends on the volume of treated adipose tissue that is deemed to be required for the later filling and/or correction procedure.

The adipose tissue withdrawing cannula is preferably introduced through the holes formed in the skin beforehand for anesthesia.

10 cc syringes are preferably used for liposuction, as they exert an adequate pressure on the tissues and allow easy handling.

These are preferably the known luer lock syringes 7, which are connected to a suction cannula having a corresponding luer connector, directly or with the interposition of special two-way valves between the cannula and the syringe, which valves, like those schematically shown in FIG. 10, are connected by a tube or a conduit 8 to the inlet 102 of the device, preferably equipped with a three-way valve 9, and allow the lipoaspirate to be directly transferred through one or more steps, from the patient into the device of the invention.

Such transfer may occur in a closed system, in which the biological material never contacts the outside environment.

The device and method as described and claimed below use the suctioned lobular fat to obtain a cell suspension with a solid phase consisting of cells, cell agglomerates having small and averagely constant sizes, and a liquid phase free from any impurity such as blood, oil, cell debris and anesthetic liquid.

As shown in FIGS. 1 and 2, the device of the present invention is composed of a washing and separating container 1 having a washing chamber 101 for washing the liposuctioned material, which container 1 has an inlet 102 and an outlet 103 for the liposuctioned material to enter the washing chamber 101 through the inlet 102 and for at least part of said material, particularly, in order of time, first the fluid component and then the solid component, to exit said chamber 101 through the outlet 103, said washing chamber 101 including means for mechanically forming an emulsion of fluid components, particularly oil obtained from broken adipocytes, blood and/or other sterile liquid solutions.

Said emulsion-forming means consist of at least one stirring element 104, such as balls or the like of equal or different sizes, for increasing emulsion of liquid components when the washing and separating container 1 is subjected to stirring. In the device of the present invention, simple manual stirring of the device can afford separation of the liquid phase composed of the fluid emulsion from the solid phase composed of cells, cell fragments, cell aggregates. Mechanical stirring may be also obviously provided, to simulate at least the manually exerted force.

These stirring elements 104 may be of relatively small size when compared with the of the washing chamber 101, because if they were too large they could not move freely in the chamber 101 and might damage the cell material contained in that chamber 101. The weight of said stirring members should also be sufficient to form an emulsion of liquids without causing cell wall breaking.

These stirring members 104 may be substantially spherical bodies, i.e. having continuous rounded exterior surfaces, and be hollow or solid, and may rotate and move within the chamber 101 to assist gentle mixing of the liquid components.

The stirring members 104 are preferably made of a sterile material that does not interact with the biological material contained in the washing chamber or with the solutions injected for washing the cell material: for example, they may be made of metal, which is easy to sterilize, even at high temperatures, and prevents the stirring members from braking or being deformed upon collision with each other or with the inner walls of the washing chamber 101.

The rounded surfaces of the stirring members 104 may also facilitate sterilization, as they prevent the creation of debris build-up areas or bacterial proliferation areas on said members 104, which would hinder cleaning and maintenance of sterile conditions. Preferably, the stirring members 104 consist of balls having a given weight and size, to facilitate mutual emulsion of liquids without causing mechanical breaking of the cell walls during manual or mechanical stirring.

The emulsion of liquids is obtained due to the presence of the stirring means 104 which enhance the mixing action, while also gently stirring the container to obtain emulsion of liquids, and preventing abrupt movements that might lead to cell breaking, such stirring not involving a disintegration of the bonds between the liquid components.

Stirring members 104 of any shape and material, such as glass, may be obviously used.

The washing and separating container 1 preferably has a cylindrical shape, but it may be formed in any shape and size that might both contain a given amount of liposuctioned fat and ensure optimal handling.

In a preferred embodiment, the lipoaspirate in the washing chamber does not exceed ⅓ of the overall chamber capacity; the remaining volume is filled with liquids.

For instance a container 1 having a 10 to 3000 cc volume may be provided.

The preferred size is a container from 300 to 600 cc, with about 100 to 250 cc lipoaspirate being treated therein.

As shown in the figures, the washing and separating container 1 is composed of a central tubular portion 111 with the washing chamber 101 formed therein, and two closing terminals 112, 113 at the ends of said tubular portion 111 such as caps 112, 113 or the like, the inlet 102 and outlet 103 of the washing chamber 101 of the washing and separating container 1 consisting of a hole formed in each cap 112, 113, communicating with a connection terminal 1021, 1031 and/or closing valves.

Obviously, said terminals 1021, 1031 and/or said at least one inlet 102 and outlet 103 may be designed to be closed with sterile caps and/or be equipped with backflow preventing means, such as one-way valves, during the step of injecting and pressing fat into said container 1.

For instance, said inlet 102 and/or outlet 103 and/or said connection terminals 1021, 1032 may be connected to three-way valves 9 like those schematically shown in FIG. 10.

The fat material is injected into the washing chamber 101 of the container 1 through the opening 102 which is equipped, for instance, with a luer connector 1021 and/or a three-way valve 9.

Male, female and neutral luer connectors are known, and allow fluid-tight connection between two devices having said connectors. Luer connectors are sold, for instance, by GVS, in their Web site www.gvs.com. Examples of syringes with a two-way valve are shown in www.internationalpbi.it.

At least one filter 4 may be provided in the washing chamber 101 of the washing and separating container 1 proximate to the outlet 103 which allows the passage of the fluid component and/or the solid component of the fat and retains the stirring elements 104 in the washing chamber 101.

In a variant embodiment of the present invention, said filter 4 may consist of a selectively permeable membrane that allows the passage of at least part of the liquid phase, consisting of an oily component, a blood component, sterile solutions such as anesthetic liquid and/or saline and retains the solid cell phase, consisting of cell fragments, whole cells and cell agglomerates, thereby allowing separation of the liquid phase of the emulsion from the solid phase.

Said selectively permeable membrane may consist of a net of fine meshes, which is smooth, i.e. with no projecting parts or irregular or sharp surfaces that might damage cell walls, whose meshes or through interstices are smaller than the cell agglomerates contained in the washing chamber 101 of the washing and separating container 1.

The meshes of the net that forms the selectively permeable membrane may have a size ranging from 1000 to 50 μm.

Such filter 4 is used to retain the stirring members 104 in the washing chamber 101 and prevent them from clogging the outlet 103 during washing and separation of the solid cell component from the emulsion.

In one preferred embodiment, as better described hereinafter, said filter 4 is replaced by a fine mesh cutting net that provides means for reducing the size of the solid component of the lipoaspirate that comes out of the washing chamber 101.

In one embodiment, at the opposite end, i.e. at the inlet 102, size reducing means may be provided for reducing the size of the solid component of liposuctioned fat 3, particularly cell macroagglomerates, to smaller cell agglomerates, i.e. having a size equal to or smaller than a given value, which means consist of at least one series of parallel or intersecting sheets or cutting wires made of sterile material, e.g. metal, to form at least one size reducing net, through which the liposuctioned material is passed before entering the washing chamber 101 of the washing and separating container 1.

The container may be made of sterile plastic or glass, or anyway of a translucent material preferably resistant to high temperatures and autoclave treatable, for injection therein of the liposuctioned fat.

As shown in FIGS. 4 and 5, said size reducing net for cell agglomerates 3 is subtended in the washing chamber 102 proximate to the inlet 103 of the washing and separating container 1 in a position substantially perpendicular to the direction of the flow of fat entering the washing chamber 101 of said washing and separating container 1.

In a preferred embodiment of the present invention the sizes of the lipoaspirate are progressively reduced.

Such progressive reduction is obtained by forcing the lipoaspirate at least once through the meshes or apertures of two or more size reducing nets at a given distance from each other.

In addition to the net proximate to the inlet 102, the washing and separating container 1 has a second size reducing cutting net 6, subtended in the washing chamber 101 proximate to the outlet 103 of the washing and separating container 1 in a position substantially perpendicular to the direction of the flow of fat exiting from the washing chamber 101 of said washing and separating container 1, so that the lipoaspirate that enters the washing and separating chamber 101, before exiting from said chamber 101, may flow through two nets with progressively finer meshes, the coarser meshes being provided in the net located proximate to the inlet 102.

Therefore, the two nets are located at a given distance from each other; particularly, they are located at the end sides of the washing and separating container, separate from the washing and separating chamber 101 that contains the stirring means 104 as well as a sufficient space to form an emulsion.

Considering the direction of the flow of lipoaspirate, the first net 3, i.e. the one located proximate to the inlet 102, stops the fibrous components of the fat lobules and performs a first small reduction, e.g. provides cell agglomerates of a relatively homogeneous maximum size, i.e. having a diameter from 0.5 to 2 mm, whereas the second net 6, located proximate to the outlet 103, performs a further reduction of the agglomerates, that have been previously washed. For example, the agglomerates and/or the cells that come out on the washing and separating container 1 may have a diameter of up to 10 um.

The second net 6, as a replacement of the filter 4, may be used to hold the stirring members in the washing and separating chamber.

Such progressive reduction through the cutting meshes of multiple nets provides a solid component to be injected which is composed of agglomerates of very small diameter and, if needed, of individual cells.

The device of the present invention allows the lipoaspirate to be reduced to transplantable material of any size.

As the cell material passes through the second net 6 located proximate to the outlet 103, after the washing step performed in the washing and separating chamber 103, said net having meshes or apertures of reduced size, it may lead to oil formation, due to the break of adipocytes.

This oil may be removed by transferring the cell material into another container 1 having a washing and separating chamber 101, with or without size reducing means.

As an alternative to or in combination with such transfer into a second washing and separating container, any residual oil/liquid may be removed by settling and/or centrifuging the treated material that comes out of the washing and separating chamber one or one and is placed in special containers.

These containers may be one or more syringes held in a syringe holder.

As shown in FIGS. 12a and 12b, the nets located, with known techniques and means, proximate to the inlet and outlet of the washing and separating chamber 101, may have honeycomb cutting meshes.

In one embodiment, the area of each mesh of the net proximate to the inlet 102, is about 4 mm$^2$, whereas the area of each mesh of the net proximate to the outlet 103 is about 1 mm$^2$.

The reduction and homologation of the cell agglomerate size are provided by the sheets or the meshes of the net or preferably the two cutting nets located in the container 1.

Each net has equal meshes or through interstices, having a diameter that ranges from 2000 μm to 50 μm, preferably from 1500 μm to 100 μm.

Since the meshes of the net 3 located proximate to the inlet 102 are larger than the meshes of the second net 6 located proximate to the outlet 103, a first size homologation and/or reduction of lipoaspirate agglomerates is obtained by passage through the meshes of the first net 3, and a second increased reduction is obtained when the material is caused to exit from the container 1, by being passed through the meshes of the second net 6.

In one embodiment, the interstices (meshes, apertures) of the size reducing means for cell agglomerates, particularly in the net 6 located proximate to the outlet 103, have a diameter ranging from 750 to 50 µm and anyway sufficient to allow the passage of cell material, even of individual cells.

Obviously, lipoaspirate size reduction and/or washing may also not occur using a single washing and separating container 1, having size reducing means therein, i.e. one, two or more nets, but using a succession of two or more containers 1, adapted to be connected together. The meshes of the net/s 3, 6 of each container 1 may have different sizes from the meshes of the net/s located in another container 1 and/or the meshes of the net or nets of a container may have different sizes from each other.

Therefore, for progressive size reduction of lipoaspirate agglomerates, the material may be forced out of a device into a second device with a washing and separating chamber 1 and size reducing means having smaller meshes then the net or nets located in the previously used device.

As shown in FIGS. 6 and 7, at least one size reducing net for cell agglomerates 3 is subtended between an inlet 202 and an outlet 203 in a reducing chamber 201 of a fat size reducing container 2, proximate to said inlet 202 of the size reducing container 2 for receiving the fat entering said reducing chamber 202, said container 2 also having an outlet 203, for the liposuctioned fat to be injected through the inlet 202, passed through the size reducing net 3 into the reducing chamber 201 of the second container 2 and allowed to exit from said reducing chamber 201 through the outlet 203, said outlet 203 being designed to be connected to the inlet 102 of the separation and collection container 1 to provide communication between the size reducing chamber 201 of the size reducing container 2 and the washing chamber 101 of the washing and separating container 1.

Alternatively and preferably, the multiple step reduction may occur by collecting the cell material into syringes, e.g. 10 cc syringes, and using the latter to introduce the material into a second complete device having progressively finer meshes.

As shown in FIGS. 6 and 7, the size reducing container 2 may be composed of two portions and half shells connected together, at least one of said two portions, preferably the portion with the outlet 203, having an inner chamber 201 for collecting the size-reduced fat.

In one embodiment, said collecting container 2 may be designed to be composed of two elements similar to the closing terminals of the washing chamber as described herein.

The two terminals may be connected to each other in a fixed or removable manner, to form a size reducing container 2 with an inner size-reducing chamber 201.

Like the washing and separating chamber 1, the collecting container is preferably of disposable type or may be removed for sterilization of the internal elements and reuse.

Obviously, the size reducing chamber 201 maybe allowed to have various sizes, to collect various amounts of size-reduced cell material, passing through at least the size reducing net 3.

Proximate to the outlet 203 a further cell agglomerate size reducing net may be provided.

Particularly, two lipoaspirate size reducing nets may be provided in the size reducing container 2, one proximate to the inlet 202 and the other proximate to the outlet 203, said two nets having meshes of different sizes: particularly, the net proximate to the inlet 202 has a larger meshes then the net proximate to the outlet 203. According to a variant, the device of the present invention is composed of at least one size reducing container 2 and at least one washing and separating container for separating the fluid component from the solid component, said size reducing container 2 having a size reducing chamber 201 with an inlet 202 and an outlet 203 and a size reducing net 3 therebetween, the outlet 203 having removable fluid-tight connection means 2021, 2031 for connection with mating connection means 102 situated at the inlet 102 of the washing chamber 101 of the washing and separating container 1.

As shown in FIG. 7, the size reducing container 2 has an inlet 202 and an outlet 203 and a size reducing net 3 for the cell agglomerates that form the solid component of fat, located in an intermediate position between the inlet 202 and the outlet 203 or offset toward the inlet 203, and the downstream compartment, with reference to the direction of injection of fat, acts as a collection chamber for the size-reduced material 202, said compartment having a predetermined volume.

The inlets 102, 202 and outlets 103, 203 of the size reducing container 2 and/or the washing and separating container 1 have removable fluid-tight connection means, such as luer connectors or the like, for connection to medical devices, such as syringes, bags or the like, having removable fluid-tight connection means compatible with the means located at the openings 102, 202, 103, 203.

Obviously, the inlets 202 and outlets 203 of the size-reducing container 2 may be designed to be closed with sterile caps and/or be equipped with backflow preventing means, such as one-way valves, during size reduction.

In order to allow the liposuctioned fat to flow into and out of the size reducing chamber 201 of the size reducing container and/or the washing chamber 101 of the washing and separating container 1 and to allow removal of the fluid component, i.e. the emulsion obtained by mechanical stirring from the washing chamber 101, means are provided for compressing or aspirating the fluid component and/or the solid component of fat, such as syringes or the like, which means can be removably and fluid-tightly connected with the mating means 1021, 1031, 2021, 2031 located at the inlets 102, 202 and the outlets 103, 203 of the size reducing chamber 201 and/or the washing and separating chamber 101.

Obviously, the flow of fat material through the meshes of the size reducing net 3, 4 may be facilitated by mixing said fat material with liquids, particularly a saline.

The size reducing net/s 3, 6 in the washing and separating container 1 and/or the net/s 3 in the size reducing container 2 may be each designed to have interstices or meshes of different sizes, so that the nets in a container have meshes of different sizes from each other and/or from the meshes of the net/s in another container, so that the cell agglomerate size reduction aimed at obtaining cell agglomerates equal to or smaller than a given value, occurs in multiple steps through the nets in said containers 1 and/or 2.

Therefore, the purpose of this part of the device of the invention is to reduce the size of adipose tissue lobules by forcing them through a special cutting net or parallel cutting sheets, preferably through two nets, and form a cell suspension with cells and/or cell agglomerates, particularly adipocytes, having reduced and averagely uniform sizes, or anyway agglomerates having equal or smaller sizes than a predetermined value, said cell suspension being adapted for use in a later transplantation step using particularly thin needles or cannulas, while avoiding clogging thereof.

The purpose of the size reducing net/s is also to increase the amount of peripheral stem cells that may contact the tissue to be treated after injection, which stem cells adhere to the outer surfaces of the cell agglomerates obtained by reducing the lipoaspirate mass.

With the above device, the sizes of cell agglomerates, upon passage through the size reducing means, are substantially identical and range from 2000 μm to 50 μm, preferably from 1500 μm to 100 μm.

As shown in the figures, the washing and separating container 1 is composed of a central tubular body 111 and two closing terminals 112, 113 or caps, which are or can be fixed to the ends of the central body 111.

Said central portion 111 is shown as having a cylindrical shape, but may be of any shape and size.

The washing container 101 has such a size as to allow handling thereof by one hand.

In one variant, as shown in FIGS. 2, 3, 4 and 5, a widened cup-shaped section 115 is provided at one end of the central tubular portion 111, which section is a widened axial end of said tubular portion, whose inside diameter is larger than that of the central portion 111.

One closing terminal 112 has an opening adapted to engage with the end of the central portion, whereas a second closing terminal 113 has an axial cylindrical extension 116 for engagement in the cup-shaped seat 115 of the central portion 111, by abutment against an outer annular radial abutment shoulder 117.

At the contact surfaces of the axial extension 116 of the closing terminal 113 and the widened cup-shaped portion 115 at one end of the were portion 111, and between the exterior surface of the end side of the central portion and the interior surfaces of the opening of a second closing terminal 112 in contact therewith, means for fluid-tight connection, such as o-rings or the like may be provided, which form, in combination with the above described components, i.e. the closing terminals 112, 113 and with the central portion 111, a completely sterile washing chamber 101, isolated from the outside environment. Indents and grooves may be further provided on these contact surfaces, for ensuring fixation of these terminals 112, 113 on the tubular body 111.

Said closing terminals 112, 113 may be designed to be removably fixed to the central tubular body 111, but said washing and separating container 1 may be also designed to be removable to allow separation of one or both terminals from the tubular portion 111. Therefore, this will provide a disposable washing and separating container 1, which is adapted to be sterilized also in its inner washing chamber 101, and hence to be reusable.

As shown in FIGS. 13a, 13b, 13c, the closing terminals 112, 113 and the central tubular portion may have very simple constructions: the two closing terminals may be in the form of caps fixedly or removably mounted to the ends of the tubular body 111.

These terminals may have shoulders on the side facing toward the washing chamber, to prevent deformation of the nets, that may be thin and delicate.

These closing terminals 112, 113 have apertures, such of through holes, formed at the longitudinal center axis of the tubular portion, which apertures have closing valves and/or fluid-tight connection means 1021, 1031 such as luer connectors, or snap-fit or screw connectors or the like, or multiple-way valves, providing connection of the washing chamber 101 with one or more medical devices, possibly at the same time, such as syringes, bags or the like, or with the side reducing chamber 201 of the size reducing container, through respective inlets 202 and/or: outlets 203 having mating connection means 2021, 2031.

As shown in the figures, a filter 4 is provided at the outlet 103, at the connection between the closing terminal 113 and the end side of the central tubular portion, inside the washing chamber, substantially perpendicular to the longitudinal axis of the central tubular portion 111, which filter maintains the stirring members 104 within the washing chamber 101, to prevent them from clogging any opening, particularly the outlet 133, when the washing and separating container 2 is vertically oriented relative to the ground for removal of the liquid emulsion. As mentioned above, the washing and separating container 1 may be also designed to be provided, at the inlet 102, with size reducing means 3 for reducing the size of lobular fat yielded from liposuction, into cells and cell agglomerates, particularly adipocytes and stem cells, of smaller and identical or similar sizes.

As mentioned above, instead of or in addition to the filter 4, a size reduction means for the liposuctioned material may be provided, such as a lipoaspirate size reducing net, which lipoaspirate is further divided into smaller agglomerates before coming out of the washing and separating chamber 101.

Therefore, at the connection between the closing terminal 112 and the end side of the central tubular portion, a size reducing net is provided in the washing chamber proximate to the inlet 102, substantially perpendicular to the longitudinal axis of the central tubular portion 111, which net reduces the size of a macroagglomerates to a predetermined value, which macroagglomerates are injected or pushed into the washing and separating chamber through the inlet 102.

A further size reducing net may be provided at the connection between the closing terminal 113 and the end side of the central tubular portion, in the washing chamber 101 proximate to the outlet 103, substantially perpendicular to the longitudinal axis of the central tubular portion 111.

In this preferred embodiment, the passage through their first size reducing net, proximate to the inlet 102, fragments the pieces of connective tissue of the lipoaspirate and/or provides a first coarse reduction of the lipoaspirate agglomerate size, whereas the passage through the second size reducing net located proximate to the outlet 103 provides cell agglomerates whose size is equal to or smaller than a given value, said nets having meshes of different sizes, particularly the first net, with reference to the direction of fat flow in the washing and separating container 1, having larger meshes than the second net.

The adipose tissue mass prepared by the above described device, i.e. the adipose tissue that underwent size reduction through the size reducing net/s and/or washing and separation of the solid component from the liquid component, is mainly composed of adipocytes, but also other types of perfectly healthy and viable cells that may be found in a lipoaspirate, and may be used for transplantation in face and/or body remodeling procedures.

The present invention addresses a method of treating' or' preventing injuries or diseases in a patient, particularly a method of treating volume deficiencies in the body and face, improving skin trophism and/or of biological stimulation, which method includes:
  at least one step of extracting biological material from donor areas of the patient, particularly adipose tissue extracted by liposuction,—at least one step of treating said material,
  at least one step of injecting the treated material into a patient.

Before the injection step, a step of collection and storage of the biological material may be obviously provided.

The treatment step includes at least one size reduction step for reducing the size of the extracted material and/or at least one washing and separation step for washing and separating the liquid phase from the solid cell phase, said treatment step being carried out using the device and method of the present invention.

In the present method, the donor patient is also the receiver patient in which the injection step is carried out.

Nevertheless, the donor and a receiver may also be different persons.

Obviously, the device and method for treating the tissue and the method of treating the patient may involve the use of a tissue other than adipose tissue.

An exemplary procedure for transplantation of the biological material prepared by the above device will be now described.

The material prepared using the above described device may be stored in one or more sterile containers, e.g. syringes, and allowed to settle and possibly centrifuged to separate the solid component from any residual oil or solutions.

The cell material prepared using the device and method of the present invention may be injected into any type of tissue and with any suitable procedure.

Once the receiving areas have been designed and accurately disinfected, the needle or microcannula of the syringe containing the prepared cell suspension is introduced into the subcutaneous or muscular tissue, thereby creating at three-dimensional net of tunnels for injection of very small amounts of cell agglomerates.

This step is preferably carried out using a disposable sterile blunted-end cannula with a luer connector, having a very small diameter.

The small size of the tunnels formed in the treated tissues facilitates integration of the cells, and cell agglomerates in the interstitial spaces of the subcutaneous tissue or in the muscular tissue, thereby reducing surgical trauma and facilitating quick return to normal consistency of tissues undergoing volume increasing and remodeling treatments.

Therefore, the formation of vary small-diameter tunnels in the tissues optimizes tissue volume reconstruction and/or biological stimulation results.

The reduction of fat lobule sizes by dividing such lobules into cell agglomerates affords a lager contact surface between the injected mass and the tissues being treated, thereby facilitating biological stimulation of the relevant areas and integration of the transplanted adipose tissue.

The use of these particularly thin cannulas, possibly of less than 1 mm, is allowed by the reduction of the size of the liposuctioned lobular fat, which occurs in at least one size reducing container 2 and/or at least one washing and separating container 1 having size reducing means consisting of at least one series of parallel sheets and/or at least one net of wires or thin sheets, preferably at least two nets, at least one of said two nets having meshes of very small sizes, which allow the passage of cell agglomerates or even individual cells having sizes of the micron order.

Should no fat size reduction occur, the cannulas that are used in transplantation procedures would become clogged.

As an alternative to sterile cannulas with a blunted end, helical or spiral-shaped cannulas 5 having a pointed or blunted end like the one as shown in FIG. 12 may be used for transplantation of adipose cells.

A helical cannula 5 is particularly useful for injection into organs in which a few penetration steps of the transplantation needle are required: the corkscrew needle affords maximized cell material density deposited along a single path. Such type of cannula allows transplantation of adipose tissue cell agglomerates even in high-consistency tissues or particularly delicate tissues, such as scar tissue, bone, cartilage, myocardium or in other organs, through a single injection point that allows treatment of a certain volume of tissue.

The cannula is introduced with a rotary motion to allow the helix to enter the tissue. Then, the cannula is extracted in the same manner while injecting cell agglomerates or clusters of adipose tissues. This will considerably increase the amount of transplanted adipose tissue per unit volume, as compared with individual injection by a rectilinear needle, and hence the volume of treated volume without reducing the contact surface between the injected adipose tissue and the receiving tissue thereby increasing the vascularization potential of injected cells, as the adipose tissue is released as strips or very thin beads of cells, due to the small diameter of the cannula, and in a spiral path.

The use of these cannulas, that allow the prepared adipose tissue, containing, in addition to adipocytes, other types of cells including stem cells, to be released in a spiral path into the tissues to be treated, is particularly suitable when there is no way to perform Coleman filling, i.e. to form a net of tunnels in the tissue to be treated due, for instance, to excessive consistency of the tissue to be treated, or when tissue trauma is undesired, such as in myocardium treatment. The present invention also relates to a tissue for transplantation, e.g. for autotransplantation or heterotransplantation, which tissue is composed of cells, possibly cell fragments and/or cell agglomerates, and is obtained using the above described device and/or method.

The tissue is composed of cell material of uniform size, with average diameters ranging from 10 μm to 2 mm.

Preferably 0.05 to 1.5 mm, especially about 0.75-0.5 mm or less (up to 10 μm).

If needed, the present device may also provide tissue composed of individual cells.

In a preferred embodiment, the tissue is an adipose tissue mainly composed of adipocytes and stem cells.

Said stem cells are adapted to be used to create any cell type, such as chondrocytes, osteocytes, adipocytes, nerve cells.

After preparation, this adipose tissue has a small liquid fraction, free of any impurity, which is mixed with cell agglomerates and is sufficient to facilitate introduction of the cells into the tissues to be treated.

Said liquid fraction may be about 50% by weight of the adipose tissue prepared for transplantation.

The present invention also obviously relates to a tissue having one or more of the above characteristics, but other than adipose tissue.

The present invention also relates to a preferably sterile and disposable kit, adapted for use both in outpatient and surgical settings.

The device or kit of the present invention has two- or three-way connectors, with or without valves, connection tubes and syringes, and various containers (e.g. a bag for the washing saline and a bag for collecting washing waste).

The kit may be used to treating cell material of any type, preferably fat for auto- or hetero-transplantation 1 and comprises at least one container 1 for washing the solid component of fat and separating said solid component from the fluid component, said washing and separating container 1 being formed as described above.

This kit, which is composed of at least one washing and separating container having size reducing means in the washing chamber 101 is particularly advantageous when used in the field of cosmetic treatment, e.g. in outpatient settings, as it provides a simple perfectly sterile device, to be used for quickly treating the material extracted from the patient, with no risk of cell material contamination due to contact with the outside environment.

The kit allows treatment of biological material, from the first tissue suctioning step to the last injection step, in a completely closed system, which allows the material to be treated without causing it to ever contact the outside environment and/or without using means that might contaminate it.

This is allowed through the use of one or more tubes, syringes, bags, multiple-way valves, luer connectors and obviously one or more washing and separating containers 1 (and possibly one or more size reducing containers 2), which are sterile and connected or connectable together in a fluid-tight manner.

Therefore, the system that provides withdrawal of biological material, treatment of the material, storage, injection of the biological material is a system that is completely isolated from the outside environment in all of its steps, from withdrawal from the patient to injection into the receiving patient.

One or more of the system components may be mechanized by connection to special equipment, so that one or more steps of the process that includes suctioning and/or treatment of the biological material and/or injection may be carried out without requiring any action by an operator.

This kit is particularly suitable for minor aesthetic surgery procedures. In one preferred embodiment, the kit comprises one or more containers 1 having at least one size reducing net, preferably two size reducing nets, as described above. Each container 1 of the kit may be designed to have nets with meshes of different sizes from those of the other containers 1 so that, by forcing the material through the meshes of the nets of multiple containers, cell agglomerates are progressively size-reduced to the desired value allowing transplantation.

Such progressive reduction avoids the risk of clogging the meshes of the nets and prevents the treatment process from being slowed down.

As an alternative, a kit may be provided which comprises:
at least one container 1 for washing the solid component of fat and separating said solid component from the fluid component, possibly having at least one size reducing net or sheets 3,
at least one size reducing container 2 formed as described above and adapted to be connected to said container 1.

In one embodiment, the kit has two or more size reducing containers 2, which are adapted to be alternately connected by their outlets 203 or inlets 202 to the inlet 102 or outlet 103 of the washing and separating container 1, a predetermined amount of fat of reduced size being stored and preserved in sterile conditions in the reducing chamber 201 of each size reducing container 2.

A kit having a set of size reducing containers 2 may be also provided, which is composed of at least two size reducing containers 2 having different sizes in terms of the meshes of the size reducing net 3 and/or the volume of fat of reduced size contained in the reducing chamber 201.

For example, the kit may be designed to contain two or more size reducing containers 2 having size reducing means 3 through which the cell material may be forced, each having a net 3 with meshes of different sizes.

The provision of two or more size reducing containers 2 allows treatment of a large amount of fat with no risk of clogging the meshes of the size reducing net and hence of slowing down the material treatment process.

The washing and separating containers 1 and/or the size reducing containers 2 may be of disposable type or may be formed in such a manner as to allow complete sterilisation and later reuse thereof.

The kit of the present invention may also include, alternatively or in combination:
one or more disposable sterile syringes with different volumes,
one or more sterile pointed needles or sterile lanceolate blades of different particular sizes to allow transcutaneous introduction of cannulae for anaesthesia, removal and transplantation,
one or more disposable sterile cannulae having a pointed or blunted end, at least one of which has a very small diameter, of the order of 1 mm,
one or more, one- or multiple-way valves, with or without check valves, e.g. three-way valves to be connected to the inlets 102, 202 and/or outlets 103, 203 of the containers 1 and/or 2,
one or more sterile tubes with luer connectors, allowing the passage of biological material from one component of the kit to another (e.g. from the syringe to the washing and separating chamber 1 or from a saline bag to the washing and separating chamber)
means or containers, such as syringes, to allow settling and/or possibly centrifugation of the fat material prepared using the above described the device, which fat material may be distributed into one or more sterile containers, to provide additional separation of the solid component, which floats after settling on the residual liquid/oily component to be removed before transplantation,
means for preserving the biological material so prepared and ready for transplantation, e.g. means for cryopreservation thereof in a closed environment simulating a clean room, i.e. a container having controlled conditions, e.g. in terms of particulate pollution, pressure and temperature.

As schematically shown in FIG. 10, the kit may comprise one or more devices such as one or more washing and separating and size reducing containers 1, syringes 8 for suctioning material from the patient, syringes 12 for collecting/injecting the treated biological material, washing liquid bags 10 (e.g. a bag containing saline), bags 11 for collecting waste material, which are or can be connected together by sterile tubes, multiple-way valves, luer connectors.

Instead of or in addition to said small diameter cannulas, the kit may include at least one helical or spiral-shaped cannula 5 with a pointed or blunted end allowing, as described above, transplantation of the cell mass of adipose tissue into high-consistency or particularly delicate tissues by increasing the volume of treated tissue with a single injection point.

The kit may also include an instrument for locking syringes during suction to temporarily prevent the plunger from bouncing back, e.g. during liposuction, and allow less traumatic adipose tissue suction.

The kit may further comprise a spring-biased mechanism for imparting a reciprocating motion to the syringe piston, which mechanism is connected to the two-way valve and affords quick withdrawal of adipose tissue, which adipose tissue is conveyed to the washing and separating chamber 101 without contacting the outside environment, through a tube having luer connectors at its ends.

The provision of a three-way valve at the inlet 102 of the chamber further allows injection of a washing solution into said chamber without disconnecting the withdrawing syringe.

The syringes in the kit may be made of plastic, preferably with a luer connector, or the like, and have various volumes.

The following may be used, by way of example:

10 to 60 cc syringes for local anesthesia injection, 5 cc syringes with needle for creating a wheal of anesthetic, 10 cc or larger volume syringes, connected to sterile 1.5 to 3 mm diameter cannulae for drawing adipose tissue from donor areas, 1 to 5 cc syringes for tissue transplantation.

Therefore, the treating method that may be carried out with the device of the present invention allows preparation of an adipose extract, e.g. obtained by liposuction, which is in the form of a mixture of fluid materials and cell fragments and one or more cell macroagglomerates of heterogeneous sizes, in a cell suspension containing cell agglomerates, particularly adipocyte agglomerates, with smaller and identical or similar sizes, in any case, smaller than a given value, to allow transplantation into areas of the face or body of the patient, requiring a filling procedure with minor trauma, and accompanied by biological stimulation of the tissues involved in the procedure.

The method may be carried out in a closed system to avoid contamination of the cell material before administration thereof to a patient.

Obviously, the adipose tissue to be transplanted may be obtained not only by liposuction but also using other known techniques.

As described above, agglomerates may be obtained with an average size of 500 μm, or smaller, i.e. about 100-10 μm, depending on the sizes of the meshes or apertures of the size reducing means that was used for liposuctioned material size reduction.

Therefore, the preparation of fat material involves the division of said fat material into cell fragments, cells or cell agglomerates that are smaller than the suctioned macroagglomerates.

Such division, as mentioned above, enhances the activity of stem cells, as it creates a favorable microenvironment facilitating contact of the stem cells with the tissue in which transplantation occurs.

In the present invention, for the cell agglomerates to be divided to sizes equal to or smaller than a given value, progressive reduction of lipoaspirate size is preferred, which means that fat is forced at least once through at least one cutting net of intersecting or-parallel wires or sheets, preferably through two nets located at a given distance from each other, said nets having meshes of different sizes.

Before and/or after size reduction, the fat may be obviously washed once or multiple times with a sterile washing solution.

The cell agglomerates so obtained undergo an additional treatment, which involves washing with sterile solutions and separation of the cell component from the liquid phases, i.e. blood, oil that comes out of the break of adipocytes, any anesthetic solutions in use, and the solution in which said agglomerates have been mixed, e.g. a saline.

Washing and separation are allowed by the use of a container 1 with a washing chamber containing stirring members 104 such as balls or the like which, by stirring the container 1, can form an emulsion of the liquid components contained in said washing chamber.

Washing of cell agglomerates in one or more washing and separating containers may continue until the liquid waste phase that comes out of the outlet 103 is perfectly clear.

Advantageously, since progressive size reduction of the lipoaspirate is obtained by forcing it through at least two nets located at a given distance from each other in a washing and separating container, i.e. at the ends of the central tubular portion, cell agglomerates are washed a first time after a first step of separation of adipose tissue lobules or macroagglomerates and reduction/homologation of the sizes of said agglomerates below a predetermined value, since the passage through the adipose tissue size reducing means 3, which is obtained by applying pressure on said adipose tissue, may cause the cell walls of adipocytes to break, with the formation of oil that has to be removed from the cell suspension containing cell agglomerates, to ensure successful transplantation of said tissue.

One or more later washing steps will be performed after a second or later size reducing steps, for obtaining a solid component of adequate size for transplantation.

Washing and separation of the cell component from the liquid phase of the extracted fat in the above described container 1, may also occur before the cell aggregate size reduction steps.

The method of the present invention includes, instead of or in addition to the dividing step, at least one step of washing the cell aggregates, which is carried out at the same time as a step of separating the fluid component, in emulsion form, from the solid component.

FIGS. 8*a*-8*d* and 10 schematically illustrate the method.

In a first step, area is exhausted from the washing and separating container 1, and the whole inner volume is filled with a liquid.

For example, the air to be exhausted before use of the device may be removed by aspirating saline with the syringe 7, by causing it to enter the bag 10 by gravity and by causing air to exit from the syringe 12 (after removing the syringe cap) and/or from the container 11 (which may be equipped with an openable exhaust valve).

The washing and separating container 1 is vertically oriented with the outlet 103 open and facing upwards: liquid is introduced into the container 1 and air is exhausted therefrom through the inlet 102.

The liquid may be a saline contained in a bag 10 connected via a tube to the opening of the chamber, which has a three-way valve.

Then, the lipoaspirate is injected into the washing and separating chamber 101.

The lipoaspirate may be injected directly from the suction syringe of the container 1 or through a completely closed system as shown in FIG. 10.

Syringes of any volume may be used. 10 cc syringes are preferred.

The fat material is injected into the chamber 101 through a suction syringe used for withdrawal, e.g. a two-way syringe equipped with a valve, directly or through a tube connected to the syringe and to the opening of the container and the fat material is pushed into said chamber by the pressure action exerted by the piston of the syringe.

In this step, the container is preferably held in a vertical position with the outlet 103 facing downwards, to the ground.

The presence of size reducing means proximate to the inlet 102 provides a first lipoaspirate size reduction/homologation.

A hydraulic force may be applied to the fat material by a washing fluid under pressure, which is injected into the washing and separating chamber 101 and forces the fat material into and out of the washing chamber 101.

The adipose agglomerate injected into the separating and washing container 1 through the inlet 102, may be repeatedly washed by pressure injection of liquid materials such as sterile salines into said inner washing chamber 101 to obtain a high-purity cell agglomerate, free of any oil, blood and of any solution used during withdrawal.

The washing and separating step in which said fluid materials are separated from said agglomerates occurs by:
- at least one injection of a sterile washing solution, e.g. saline, into the washing chamber 101 containing the fat material, of a washing and separating container 1, which washing chamber 101 contains at least one stirring element 104. In this step, the container is held in a vertical position with the outlet 103 facing toward and parallel to the ground
- manual or mechanical stirring, manual stirring being sufficient, of said washing and separating container 1 to facilitate emulsion of fluid components, particularly the oily component and blood with the sterile fluid substances; the emulsion being formed by orienting the washing and separating container in a horizontal position, i.e. approximately parallel to the ground (Figure Bb),
- arrangement of the washing and separating container 1 in a vertical position relative to the floor, with the outlet 103 facing downwards, to obtain a stratification of the solid components on the liquid emulsion which constitute the fat contained in the washing chamber 101, particularly to obtain a solid component composed of cell fragments, cells and one or more cell agglomerates floating on an emulsion of the fluid components in the lower portion of the washing chamber 101 in contact with the outlet 103 of the washing and separating container 1,
- discharge of the emulsion of fluid components (i.e. oils/liquids) from the washing chamber 101 through the outlet 103 of the washing and separating container 1 (FIG. 8c). The emulsion is forced out by injection of washing fluid through the opening 102, with a given pressure.

Since the container has a cylindrical shape, its horizontal position means that its longer axis passes through the end sides parallel to the ground, whereas its vertical position means that the cylinder is oriented with its longer axis perpendicular to the ground.

The emulsion is collected in another container 11 which is fluid-tightly connected by suitable means to said opening 103, to prevent contamination of both the outside environment and the cell material contained in the chamber 101.

Therefore in the washing step, the washing and separating container 1 containing fat mixed with a sterile solution, e.g. either saline injected with a syringe through the inlet 102 or saline withdrawn from a bag, is stirred with a force that does not cause the cell walls to break but is sufficient to form an emulsion, i.e. a dispersion of tiny oil drops within the washing fluid, due to the presence of the balls 104.

The container is stirred to form the emulsion with the container 1 horizontally oriented.

Obviously in this step the openings, i.e. at least one inlet 102 and/or one outlet 103 of the container 1 are closed to prevent any leakage of material.

At the end of the container stirring step, the container is moved to a vertical position and the different densities of the materials that form the lipoaspirate create one solid layer of cells and cell fragments in the washing chamber 101, which layer floats on the emulsion of liquids.

The washing step is repeated by injecting sterile washing solutions into the chamber, with subsequent emulsion formation (by stirring the container with the inlet and the outlet closed) and discharge of the emulsion (by the injection of a clean washing solution), until the outflowing liquid-oil-blood emulsion appears to be free of any impurity such as blood and oil.

Therefore, the discharge of fluid component emulsions may be repeated.

Such discharge of the emulsion is obtained by the flow of a physiological liquid caused by gravity, which flow allows removal of liquid components (oil/liquid) through a density gradient, at least for a given time interval, i.e. until there is emulsion between tiny oil drops and liquid, which is sufficient each time, i.e. for each washing cycle, to remove a considerable amount of waste liquids (particularly oil).

The water/oil emulsion is eliminated from the container through a density gradient, following the outflowing liquids (the flow from the inlet 102 to the outlet 103) obviously provided that said washing flow is sufficient.

As shown in FIG. 9, the oil/liquid emulsion is discharged.

Oil can be discharged as long as it is part of an emulsion.

What is discharged is an emulsion of tiny oil drops and washing liquid.

The cell mass floats on said emulsion.

Therefore, the emulsion is required to allow elimination of impurities, such as oil, in the lipoaspirate.

At the end of the washing step, the solid component floats on the clean washing solution.

Therefore, at the end of the washing and separating step, the material in the chamber 101 of the container may be used for transplantation.

Adipose tissue washing is an important step, as it allows removal of oil resulting from the break of the cell walls of adipocytes during mechanical withdrawal of adipose tissue, using cannulas or needles, from donor areas and during passage of fat, under pressure, through the size reducing net 3.

The solid component does not remain in the device 1 but is recovered, preferably after further size reduction performed at the outlet 103, by a hydraulic thrust exerted from the inlet 102.

The solid component is discharged from the washing and separating container by vertically orienting said container with the outlet 103, with a size reducing net 6 preferably provided proximate thereto, facing upwards, so that the solid component floats on the washing solution (FIG. 8d).

Therefore, the solid component to be discharged is located next to the outlet 103.

The solid component is pushed out through the second net 6, by injection of the washing solution through the inlet 102.

It was found that what is discharged is first an aqueous solution with little cell material, then a solution rich with cell material and finally a solution with little cell material.

One or more containers may be connected to the outlet 103, one after the other, for instance syringes 12, for collecting the prepared biological material mixed with liquid.

Such material has undergone further reduction/homologation through the net 6.

The container 12 are allowed to settle to obtain the separation of the solid component from the residual liquid component.

Instead of or in addition to the above, separation may occur by centrifugation.

The biological material so prepared is preserved or preferably cryopreserved in a closed environment, simulating a clean room.

Obviously, the material stored in the container 12 may be designed to be treated again in a washing and separating container 1 and/or a size reducing container 2, before being finally preserved and/or reinjected.

The whole material treating system is closed, from withdrawal from the patient to reinjection. This characteristic is particularly important for banking of biological tissues, i.e. preservation thereof in biological banks.

Therefore, the biological material conveyed into the container 12 has always been in a sterilized close system, never in contact with air.

Thus, said material may be directly cryopreserved with no further change requesting the use of a clean chamber.

As described above, multiple mutually connectable washing and separating containers may be provided, for progressive reduction and/or washing of the lipoaspirate.

The device of the present invention allows simple, quick and inexpensive treatment of cell extracts in the form of cell macroagglomerates mixed with a liquid phase, which provide cell aggregates of substantially identical whole and viable cells of predetermined size, anyway smaller than a predetermined value, which agglomerates are separate from the liquid component, in the form of emulsion, containing waste liquids. These agglomerates may be used for transplantation.

Obviously, the material yielded from treatment of adipose lobules may contain not only cell aggregates but also individual cells and cell fragments to be used as a biological filler.

Furthermore, the liposuctioned material contains not only adipocytes but also other types of cells, such of stem cells.

The treating method implemented by the device does not involve the use of enzymes or other components that can have a chemical action on the liposuctioned material, or a biological action on agglomerate composing cells, but uses the possibility of changing the size of cell agglomerates, to obtain a larger exposed cell surface, that may contact the tissues treated during transplantation. Particularly, solid material for injection is provided, which also forms an optimal in vivo microenvironment for the action of stem cells in the areas in which said treated material is reinjected, which stem cells are contained in the suctioned material.

Therefore, the method of the present invention simply and inexpensively provides biologically active injectable biological material from the material extracted from the patient, also due to the presence of stem cells, and requires neither the use of chemicals such as emulsifiers or enzymes, nor in vitro culture steps. Furthermore, these very small cell agglomerates may be transplanted using very thin cannulas, which reduce surgical trauma and optimizes tissue integration.

Also, the use of a device of the present invention provides a closed system that isolates the biological material from the outside environment and allows it to be prepared for use in a very short time, thereby reducing possible contamination risks.

The device, kit and method as disclosed above, which form the subject of the present invention, may be obviously used not only for preparing adipose tissue to be transplanted, but also for preparing any type of cell agglomerate that is required to have a high purity level for use.

I claim:

1. A method of preparing adipose tissue for transplantation from lobular fat material extracted from a body by liposuction, said method comprising:
   providing a device comprising at least one washing and separating container having a washing chamber for washing liposuctioned fat material, said container having an inlet for liposuctioned fat material to enter the washing chamber, and an outlet;
   filling an inner volume of the washing and separating container with a first sterile washing solution;
   injecting liposuctioned fat material into the washing chamber of the container through the inlet, said liposuctioned fat material comprising (a) a fluid component comprising one or more of an oily component, and a blood component, and (b) a solid component comprising tissue fragments and one or more cell macroagglomerates of heterogeneous size;
   forming an emulsion of the fluid component in the sterile washing solution by means of active and/or passive stirring means; and
   washing the solid component at least once, and separating the fluid component, in emulsion form, from the solid component, wherein said washing and separating steps are carried out at the same time, and wherein said washing and separating steps include:
   injecting a second sterile washing solution into the washing chamber, thereby providing a flow of said second sterile washing solution from the inlet towards the outlet that, through a density gradient, forces the emulsion out from the outlet; and
   discharging the emulsion from the outlet through said density gradient.

2. The method according to claim 1, wherein said first and second sterile washing solution have the same composition.

3. The method according to claim 1, wherein said step of forming an emulsion comprises manual or mechanical stirring of said washing and separating container to facilitate emulsion of fluid components.

4. The method according to claim 3, wherein said washing and separating container comprises a plurality of stirring elements each having a relatively small size when compared with a washing chamber in order to freely move in the washing chamber without damaging a cell material contained in that chamber.

5. The method according to claim 1, wherein said step of separating the fluid component, in emulsion form, from the solid component comprises an arrangement of the washing and separating container in a vertical position relative to a floor, with said outlet facing downwards, to obtain a stratification of the solid components on the liquid emulsion which constitute the liposuctioned fat material contained in the washing chamber to obtain a solid component composed of cell fragments, cells and one or more cell agglomerates floating on an emulsion of the fluid components in a lower portion of the washing chamber in contact with said outlet of the washing and separating container.

6. The method according to claim 1, wherein the method does not involve the use of enzymes or other components that can have a chemical action on the liposuctioned fat material.

7. The method according to claim 1, further comprising a step of dividing said liposuctioned fat material into smaller cell agglomerates, so that said smaller cell agglomerates are as large as or smaller than a predetermined size, and so that they are on average of the same size, wherein this size reducing step is carried out by causing said extracted lobular fat to pass at least once through size reducing means located in said washing and separating container or in a size-reducing container.

\* \* \* \* \*